United States Patent [19]
Bodian et al.

[11] Patent Number: 6,080,791
[45] Date of Patent: Jun. 27, 2000

[54] METHOD OF TREATING A VIRAL CONDITION BY INHIBITING MEMBRANE FUSION

[75] Inventors: Dale L. Bodian; Judith M. White, both of San Francisco; Irwin D. Kuntz, Greenbrae; Jay F. Stearns; R. Bryan Yamasaki, both of Santa Rosa, all of Calif.

[73] Assignees: Seres Laboratories, Inc., Santa Rosa; University of California, San Francisco, both of Calif.

[21] Appl. No.: 07/919,287

[22] Filed: Jul. 24, 1992

[51] Int. Cl.[7] .................. A61K 31/12; A61K 31/045; A61K 31/05

[52] U.S. Cl. .................. 514/678; 514/679; 514/680; 514/681; 514/682; 514/728; 514/732; 514/734; 514/736

[58] Field of Search .................. 514/678, 679, 514/680, 681, 682, 728, 732, 734, 736

[56] References Cited

U.S. PATENT DOCUMENTS 4,898,891   2/1990   Lavic et al. .................. 514/732

FOREIGN PATENT DOCUMENTS 0923028   2/1983   U.S.S.R. .................. A61K 31/47

OTHER PUBLICATIONS

Bogdonova et al 73 CA 129328z 1970.
Thiel et al 84 CA 160055 1996.
Korsakova et al 96 CA:199209k 1982.
Lyubehanskaga et al 115 CA 231795x 1991.
Griueu et al 85 CA: 56546 c 1976.
Connolly, M. L., "Solvent–accessible surfaces of proteins and nucleic acids." Science 221: 709–13 (1983).
Doms, R. W., Gething, M.–J., Henneberry, J., White, J. and Helenius, A., "Variant influenza virus hemagglutinin that induces fusion at elevated pH." *J. Virol.* 57: 603–13 (1986).
Doms, R. W., Helenius, A. and White, J., "Membrane fusion activity of the influenza virus hemagglutinin the low pH–induced conformational change." *J. Biol. Chem.* 260: 2973–81 (1985).
Ferrin, T. E., Huang, C. C., Jarvis, L. E. and Langridge, R., "The Midas display system." J. Mol. Graph. 6: 13–27 (1988).
Gasteiger, J. and Marsili, M., "Iterative partial equalization of orbital electronegativity—a rapid access to atomic charges." Tetrahedron 36: 3219–88 (1980).
Goodman & Gilman, The Pharmacological Basis of Therapeutics, 7th Edition, MacMillan, (1985) at p. 1232.
Abola, E.E., Berstein, F.C., Bryant, S.H., Koetzle, T.F. and Weng, J., in F. H. Allen, G. Bergerhoff and R. Seivers (Eds.), Crystallographic Databases–Information Content, Software Systems, Scientific Applications, (Data Commission of the International Union of Crystallography, Cambridge, 1987) pp. 107–32.

Kuntz, I. D., Blaney, J. M., Oatley, S. J., Langridge, R. and Ferrin, T. E., "A geometric approach to macromolecule–ligand interactions." J. Mol. Biol. 161: 269–88 (1982).
M. Kielian and S. Jungerwirth, "Mechanisms of Enveloped Virus Entry into Cells," Mol. Biol. Med. 7: 17–31 (1990).
Mosmann, T., "Rapid colorimetric assay for cellular growth and survival application to proliferation and cytotoxicity assays." J. Immunol. Methods 65: 55–63 (1983).
Porter, R. F., Rees, W. W., Frauenglass, E., Wilgus, H. S., Nawn, G. H., Chiesa, P. P. and Gates, J. W., "The chemistry of thioether–substituted hydroquinones and quinones. I. The 1,4 addition of a heterocyclic mercaptan to quinones," J. Org. Cem. 29: 588–94 (1964).
Still, W.C., Kahn, M. and Mitra, A., "Rapid chromatographic technique for preparative separations with moderate resolution," J. Org. Chem. 43: 2923–25 (1978).
Shoichet, B. K., Bodian, D. L. and Kuntz, I. D., "Molecular docking using shape descriptors." J. Comp. Chem. 13: 380–97 (1992).
Simons, K., Garoff, H. and Helenius, A., "How an animal virus gets into and out of its host cell," Sci. Am. 246: 58–66 (1982).
Skehel, J. J. and Schild, G. C., "The polypeptide composition of influenza A viruses," Virology 44: 396–408 (1971).
Stegmann, T., Delfino, J. M., Richards, F. M. and Helenius, A., "The HA2 subunit of influenza hemagglutinin inserts into the target membrane prior to fusion," J. Biol. Chem. 266: 18404–10 (1991).
White, J. M. and Wilson, I. A., "Anti–peptide antibodies detect steps in a protein conformational change low pH activation of the influenza virus hemagglutinin." J. Cell Bio. 105: 2887–96 (1987).
White, J. M., "Viral and cellular membrane fusion proteins," Ann. Rev. Physiol. 52: 675–97 (1990).
Bernstein, F. C., Koetzle, T. F., Williams, G. J. B., Meyer, E. F., Jr., Brice, M. D., Rodgers, J. R., Kennard, O., Shimanouchi, T., et al., "The Protein Data Bank: A computer–based archival file for macromolecular structures," J. Mol. Biol. 112: 535–42 (1977).
Wilson, I. A., Skehel, J. J. and Wiley, D. C., "Structure of the hemagglutinin membrane glycoprotein of influenza virus at 3 Å resolution," Nature 289: 366–73 (1981).

*Primary Examiner*—Marianne M. Cintins
*Attorney, Agent, or Firm*—Nathan P. Koenig; Crosby, Heafey, Roach & May

[57]   ABSTRACT

A method of preventing and treating a viral condition caused by an enveloped virus is described, comprising using a therapeutically effective amount of a compound selected from the group consisting of a substituted hydroquinone and the corresponding benzoquinone, wherein said hydroquinone comprises a 2-$R^1$, 3-$R^2$-1,4-hydroquinone where at least one of $R^1$ and $R^2$ include a carbon linkage to the benzene ring of the hydroquinone. Particularly useful compounds include 5,8-dihydro-5,8-methano-1,4-naphthalenediol, 1,4-naphthoquinone, 3', 6'-dihydroxybenzo-norbornane, tert-butylhydroquinone, other diols, e.g. 1,5-naphthalenediol, and alkylated diols, e.g. 4-methoxy-1-naphthol.

28 Claims, 4 Drawing Sheets

Effect of compounds of 83 (□), 83K (♦), and 83A (■) on precipitation of BHA by SPA with the α-fusion peptide antibody.

FIG. 7

Hemolysis with compound 91 as a function of pH.
(■) samples containing 0.1 mM 91, (□) samples without 91.

FIG. 8

METHOD OF TREATING A VIRAL CONDITION BY INHIBITING MEMBRANE FUSION

ACKNOWLEDGEMENT OF GOVERNMENT SUPPORT

This invention was made in part with Government support under grant nos. GM-31497 and GM-39552 from the National Institutes of Health. The Government has certain rights in this invention.

FIELD OF THE INVENTION

The present invention pertains to a method of preventing and treating a viral condition using compounds that interfere with fusion of virus particles with a membrane of a potential host cell. The method is particularly useful for treating influenza.

BACKGROUND OF THE INVENTION

A wide variety of viral conditions affect living organisms. Many viral conditions affect the majority of humans, or other mammals, at some time in their lives. Other viruses affect a smaller but significant number of humans at some time. Many of these viruses must fuse with a host cell membrane in order to infect the cell and reproduce. Enveloped viruses include a fusion protein that changes conformation from a native form to a fusogenic form. This promotes fusion of the viral membrane with the host cell membrane, resulting in injection of viral contents into the host cell.

Influenza pandemics recur on an annual basis worldwide. Vaccination programs aimed at curtailing the spread of the disease are hampered by the fast mutation rate of antigenic sites on the virus. Medical practices abroad permit use of the drugs amantadine and rimantadine to treat influenza A infections. However, due to the potential for undesirable side effects, use in the United States is recommended only for the population deemed most at risk. The cost of millions of lives and billions of dollars each winter underscores the urgent need for development of safe and effective anti-influenza drugs.

Analysis of the replication pathway of the orthomyxovirus reveals a number of steps that can be targeted for antiviral therapy. Successful infection requires host cell recognition, delivery of the infectious genome into the host cell cytoplasm, replication of the viral genes and proteins, and escape of progeny viruses. Any of these steps is potentially susceptible to intervention. However, the antiviral strategy must be specific for influenza proteins or processes in order to avoid adventitious inhibition of normal cellular functions.

Early events in the viral life cycle leading to the deposition of the viral genes inside the cell are shown schematically in FIG. 1. Referring to FIG. 1, infection begins by binding between the hemagglutinin glycoprotein 1 protruding from the viral envelope 2 and sialic acid residues of cellular receptors 3, which triggers endocytosis (at B). As the virus is endocytosed via the normal cellular pathway it encounters progressively decreasing pH. At a threshold pH specific to the particular strain of influenza, fusion between the viral membrane and the endosomal membrane is initiated (at C). This fusion event results in release of the infectious genome 5 into the cell cytoplasm 6 (at D), where successive steps of the replication cycle can occur. M. Kielian and S. Jungerwirth, "Mechanisms of Enveloped Virus Entry into Cells," Mol. Biol. Med. 7:17–31 (1990); Simons, K., Garoff, H. and Helenius, A., "How an animal virus gets into and out of its host cell," Sci. Am. 246: 58–66 (1982).

The critical role of membrane fusion in infection makes it an attractive target for inhibition. To date, this route of antiviral chemotherapy has been largely unexplored. Inhibition of fusion has the advantage of interfering with an early step in replication, prior to penetration of the virus into the host cell. As it does not aim to inhibit an enzymatic activity or to mimic any ligands, the chance of fortuitous inhibition of unintentional targets is minimized. Since fusion is a step common to the replication of all enveloped viruses, this antiviral strategy can potentially be applied to a host of other viral diseases, including those caused by togaviruses, rhabdoviruses, paramyxoviruses, herpes viruses, and retroviruses.

Examination of fusion in more detail reveals it to be a protein-mediated event triggered by the viral hemagglutinin. Hemagglutinin is a trimer of identical subunits. Each monomer is composed of two polypeptide chains, HA1 and HA2, which are generated by proteolytic cleavage of a precursor, HA0. The polypeptides comprising the monomer are covalently linked by a single disulfide bond but the three monomers of a trimer are stabilized by noncovalent interactions only. Wilson, I. A., Skehel, J. J. and Wiley, D. C., "Structure of the hemagglutinin membrane glycoprotein of influenza virus at 3 Å resolution," Nature 289: 366–73 (1981). The chains in the trimer are sometimes described as the A, C and E chains (HA1 chains in each monomer) and B, D, and F chains (corresponding HA2 chains).

Residues 1–24 at the amino terminus of HA2 play a critical role in fusion. This segment, known as the fusion peptide, has been proposed to form a sided helix in which one face of the helix is composed primarily of hydrophobic amino acids. White, J. M., "Viral and cellular membrane fusion proteins," Ann. Rev. Physiol. 52: 675–97 (1990). While the function of the fusion peptide is not clearly understood, current evidence suggests it aids fusion by interacting with the target membrane. Stegmann, T., Delfino, J. M., Richards, F. M. and Helenius, A., "The HA2 subunit of influenza hemagglutinin inserts into the target membrane prior to fusion," J. Biol. Chem. 266: 18404–10 (1991). The fusion peptide is the most highly conserved region among influenza virus hemagglutinins sequenced to date, and hydrophobic or sided fusion peptide sequences have been identified in the fusion proteins of a wide variety of enveloped viruses. White, J. M., loc. cit.

Upon exposure to low pH, hemagglutinin undergoes an irreversible conformational change that is a prerequisite for fusion. The conformational change most likely involves a rearrangement of domains rather than major secondary structural alterations since circular dichroism measurements reveal only minor differences between the neutral and low pH forms. Studies of the conformational change have been facilitated by isolation of the soluble ectodomain of the integral membrane glycoprotein. This proteolytic fragment, BHA, is generated by bromelain cleavage of hemagglutinin at a site adjacent to the transmembrane domain. BHA has been identified as a reliable model for the complete protein (HA) in many assays not requiring membrane attachment. See White, J. M. and Wilson, I. A., "Anti-peptide antibodies detect steps in a protein conformational change: low pH activation of the influenza virus hemagglutinin," J. Cell Bio. 105: 2887–96 (1987). The term "hemagglutinin" is used to mean both HA, the intact integral membrane protein, and BHA, its proteolytic fragment lacking the transmembrane and cytoplasmic domains.

Previous studies on HA and BHA have shown that the low pH form of hemagglutinin may be distinguished from the neutral pH form immunologically, biochemically and biophysically. Only the low pH conformation is susceptible to cleavage by trypsin and by proteinase K. The low pH form of BHA has increased hydrophobic character, observed by binding to liposomes, partitioning into detergent solution or aggregation in aqueous solution. Low pH and native hemagglutinin have also been distinguished by electron microscopy.

The crystal structure of neutral pH BHA from the X31 strain of influenza (A/Hong Kong/1968; H3N2) has been solved to 3 Å resolution. Wilson, I. A., et al., loc. cit. Referring to FIG. 2, tracings of the α-carbon backbones of both the trimer (left) and monomer (right) are shown. The figure illustrates the bromelain cleavage site 11, the C-terminus 13 of chain HA1, and fusion peptide between 14 and 15. Each monomer has been described as comprising three domains: a globular head domain 12 containing the sialic acid binding site, a narrow stem composed primarily of residues of HA2, and a connecting hinge region. The fusion peptides of native hemagglutinin are buried in the trimer interface of the stem region. The conformational change is thought to release the fusion peptides from their unexposed location, freeing them to mediate fusion.

Since membrane fusion depends on the conformational change, inhibition of fusion peptide exposure should prevent fusion and all successive steps of viral replication. Therefore, the antiviral strategy was to identify a small molecule that could bind to the native form of hemagglutinin and stabilize that conformation over any fusogenic conformation. A new class of such inhibitors may provide safe and effective drugs.

SUMMARY OF THE INVENTION

The present invention is for a method of preventing and treating a viral condition caused by an enveloped virus. The method uses a therapeutically effective amount of a compound selected from the group consisting of a substituted hydroquinone and the corresponding benzoquinone, wherein said hydroquinone comprises a 2-$R^1$, 3-$R^2$-1,4-hydroquinone where at least one of $R^1$ and $R^2$ include a carbon linkage to the benzene ring of the hydroquinone. Particularly useful compounds include 5,8-dihydro-5,8-methano-1,4-naphthalenediol, 1,4-naphthoquinone, 3',6'-dihydroxybenzonorbornane, and tert-butylhydroquinone. Other compounds are useful, including other diols, e.g. 1,5-naphthalenediol, and alkylated diols, e.g. 4-methoxy-1-naphthol.

The viral condition may be caused by a virus from a family of Togaviridae, Flaviviridae, Coronaviridae, Rhabdoviridae, Filoviridae, Paramyxoviridae, Orthmyxoviridae, Bunyaviridae, Arenaviridae, Retroviridae, Hepadnaviridae, Herpesviridae, Poxviridae and Iridoviridae. Conditions which can be treated using the present method include rubella, yellow fever, rabies, influenza, Korean hemorrhagic fever, common colds, respiratory syncytial virus, measles, mumps, HIV, hepatitis B, Herpes simplex, CMV, chicken pox, smallpox, Marburg virus, Lassa fever and African swine fever.

The process of developing suitable compounds is described in detail, along with screening procedures to separate ineffective compounds from compounds suitable for preventing and treating viral conditions.

BRIEF DESCRIPTION OF THE DRAWINGS

FIG. 7 illustrates the effect of the diol versus benzoquinone forms of compound 83 on precipitation of BHA by SPA with the fusion peptide antibody.

FIG. 8 illustrates hemolysis with compound 91 as a function of pH.

DETAILED DESCRIPTION OF THE INVENTION

The compounds useful in the method of this invention were discovered through a process of rational drug evaluation. Preliminary experiments showed that one apparently reversible inhibitor, 5,8-dihydro-5,8-methano-1,4-naphthalenediol, compound 83, available from Aldrich Chemicals and purified at SERES Laboratories Incorporated as described below, showed significant activity in assays designed to detect inhibition of fusion peptide exposure. Compound 83 also inhibits HA-mediated hemolysis, virus induced syncytia formation and influenza infectivity. A series of related compounds were studied and several were identified which show significant inhibitory effect, as measured by the same tests.

The first useful compound, 83, discovered in this series was discovered as a result of a rational evaluation of hemagglutinin (HA) and compounds that might bind the native conformation of the protein trimer. Using the DOCK program, described below, compound 83 can be fit to the structure of HA near the stem region but also near the hinge region of the trimer. Since 83 showed significant activity in the SPA screening assay, a search for related or similar, commercially available compounds was initiated.

DOCK can be used to evaluate shape complementarity between compounds and is particularly useful for judging complementarity between a known or potential binding site, e.g. a receptor or pocket on a protein of interest, and target compounds such as potential inhibitors. See Shoichet, B. K., Bodian, D. L. and Kuntz, I. D., "Molecular docking using shape descriptors," *J. Comp. Chem.* 13: 380–97 (1992). There are several available databases describing commercially available small molecules. MACCS-II3D includes three such libraries, the Fine Chemicals Directory (FCD), the Molecular Drug and Data Report (MDDR), and Comprehensive Medicinal Chemistry (CMC). These databases include computer-generated three-dimensional coordinates for 75,000 chemicals.

Three HA sites were studied in detail. The first was a pocket in the stem region which is approximately bounded by residues Cys14A (residue 14 in the "A" chain), Leu 15A, Gly 16A, His 18A, Glu 325A, Ile 10B (the "B" chain, an HA2 chain, is paired with the "A" chain to form one monomer of the trimer), Glu 11B, Asn 12B, Gly 13B, Trp 14B, Arg 25B, Asn 135B, and Cys 137B. The top scoring ligands from all DOCK runs were examined graphically for their potential ability to interact with the medial hydrophobic region of the site, with the charged residues, and with His 18A at the base of the site. Compounds that placed groups within hydrogen bonding distance of hydrogen bond donors or acceptors in the receptor were also considered.

Figure 1:
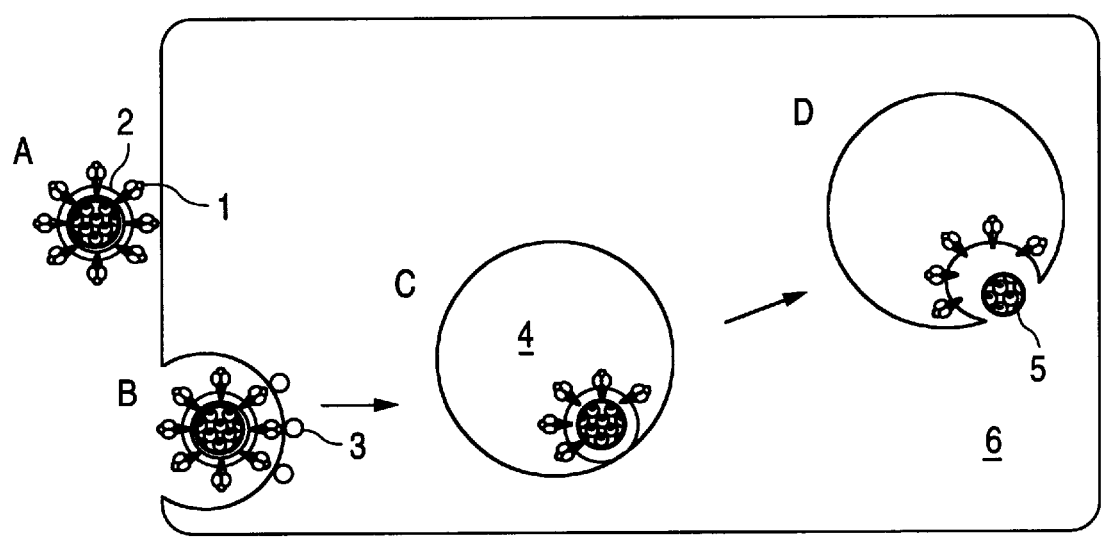
FIG. 1 illustrates endocytosis and fusion of virus particles with a host cell.
Figure 2:
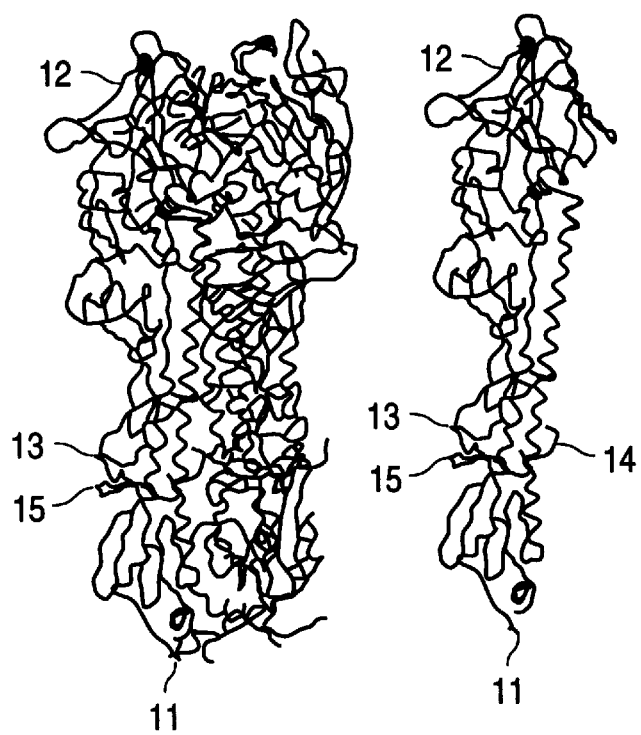
FIG. 2 illustrates the structure of BHA.
Figure 3:
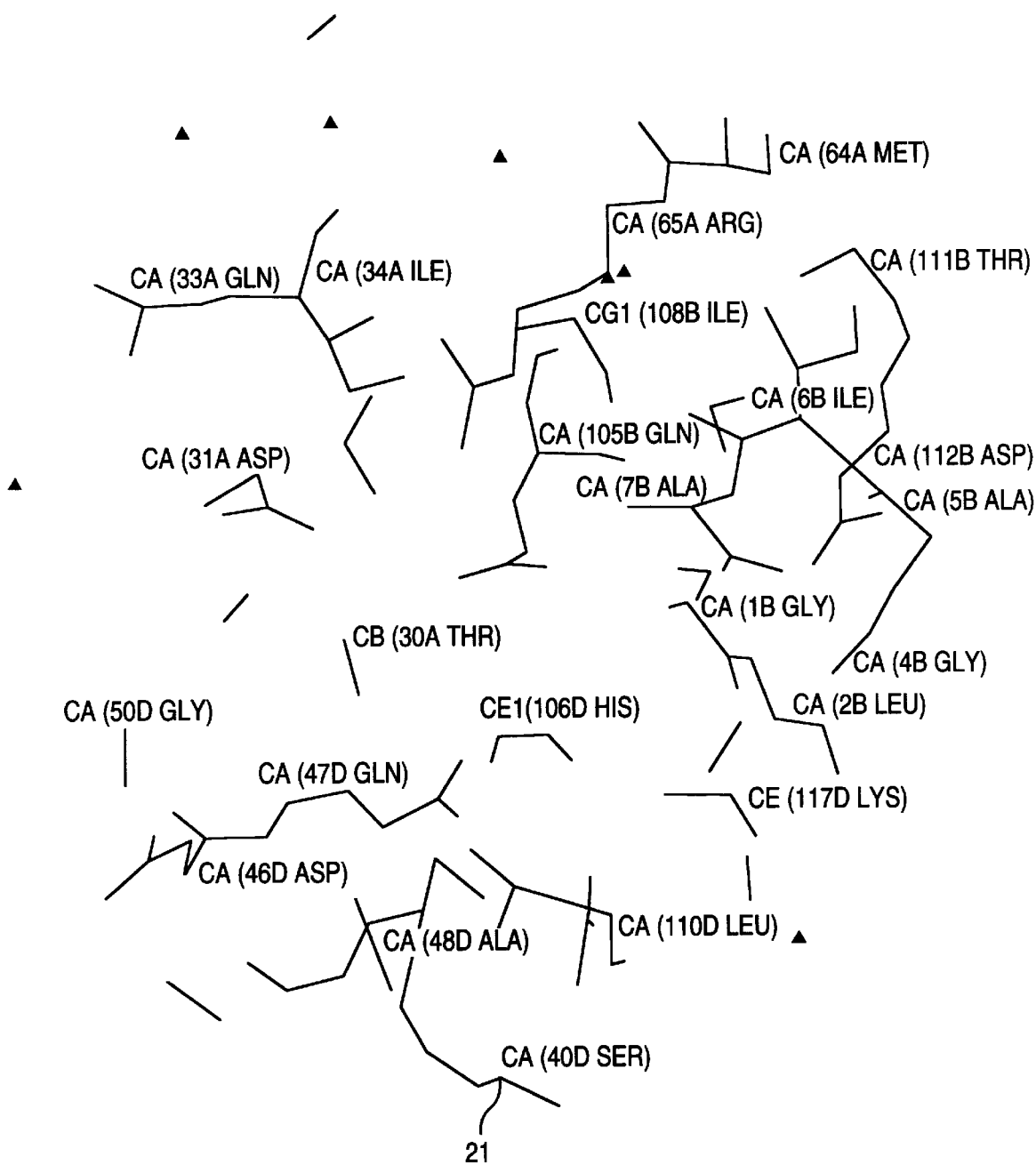
FIG. 3 illustrates the residues in and around one potential binding site adjoining the fusion peptide.

Other potential binding sites at the interface between two monomers were evaluated and a site near residue Lys 117D (lysine, residue 117 in the "D" chain) was identified. This site adjoins residues of the fusion peptide. FIG. 3 illustrates the residues bounding this site. The numbers in parentheses indicate the residue number, chain, and type of amino acid. For example, the residue 21 is serine, residue 40 in the D chain. Preliminary crystallographic results with compound 90, one of the derivatives, suggest this compound is binding to hemagglutinin at a site in the hinge region of the trimer. This site includes the following residues: Asn 296A; Tyr 308A, Val 309A, Lys 310A, Gln 311A, Asn 312A, Glu 85B, Asp 86B, Thr 87B, Lys 88B, Ile 89B, Asp 90B, Leu 91B, Trp 92B, Ser93B, Try 94B, Asn 95B, Ala 96B, Glu 97B, Leu 98B, Leu 99B, Pro 293C, Phe 294C, Gln 295C, Gly 303C, Ala 304C, Cys 305C, Pro 306C, Lys 307C, Tyr 308C, Val 309C, Lys 58D, Thr 59D, Asn 60D, Glu 61D, Lys 62D, Thr 87D, Lys 88D, Ile 89D, Asp 90D, Leu 91D, Trp 92D, Ser 93D, Tyr 94D, Asn 95D, Ala 96D and Leu 99D. The bottom of one branch within the site includes residues Lys 27A and Ile 29A. Presumably other compounds in the class also bind at that site. The exact binding site and exact mechanism of action of the present compounds has not been determined conclusively.

Note that HA is a trimer composed of subunit chains and therefore has three-fold symmetry. The binding sites just discussed in relation to one selection of trimers are "mirrored" by two other identical sites involving different specific chains. For example, the discussion above included one site in the stem region, a pocket near or including Cys14A on one of the three monomers, the A and B chains. There is a corresponding and indistinguishable site on the C and D chains and another corresponding and indistinguishable site on the E and F chains.

Applying a general scoring technique to the compounds listed in the FCD database, evaluating the goodness of fit for a test compound and the HA protein identified a field of a few thousand potential candidates. These candidates were ranked and graded on how well the compounds filled a putative binding site, toxicity (or lack thereof), commercial availability and other factors. A group of about fifty candidate compounds was identified through this search. The candidate compound, 83, identified by this process was tested and found to have significant activity. The hydroquinone analog 83A of benzoquinone 83K had significantly higher activity. The structures of all compounds discussed herein are summarized in Table 7. The conversion of 83K to 83A is described below. Note that references to compound 83 refer to 83K but without special purification.

With a target compound in hand, other compounds fitting a similar profile in terms of molecular weight, substituent groups, and polarity were identified by further comparison of database entries. A group of about forty analogs of compound 83 was identified and tested. These compounds are listed in Table 7, below. Inhibition was observed with analogs of 83 in the scintillation proximity assay (SPA), hemolysis (HEM), syncytia, and infectivity (INF) assays. The concentration profile of each compound was consistent between the various experiments, suggesting a common mechanism for inhibition of the conformational change, fusion, and infectivity.

The compounds described herein have significant inhibitory effect on membrane fusion of a model influenza-A virus. The fusion peptide is the most highly conserved region among influenza virus hemagglutinins sequenced to date, including the principal influenza subclasses A, B and C, and hydrophobic or sided fusion peptide sequences have been identified in the fusion proteins of a wide variety of enveloped viruses. White, J. M., "Viral and cellular membrane fusion proteins." Ann. Rev. Physiol. 52: 675–97 (1990). The fusogenic mechanism is highly conserved.

The compounds disclosed in this invention prevent a change to a fusogenic conformation, effectively limiting fusion of an associated virus. Such viruses specifically include members of the following families: Togaviridae, Flaviviridae, Coronaviridae, Rhabdoviridae, Filoviridae, Paramyxoviridae, Orthomyxoviridae, Bunyaviridae, Arenaviridae, Retroviridae, Hepadnaviridae, Herpesviridae, Poxviridae and Iridoviridae. See Fields et al., VIROLOGY, 2d Edition, Volume 1, Raven Press (1990) at Chapter 1.

The following table lists some characteristics of these viruses and representative disease states caused by these viruses.

| Virus Family | Fusion Protein | Fusion Peptide | Conf. Change | Host Species | Representative Disease States |
|---|---|---|---|---|---|
| Low pH Fusers | | | | | |
| Togaviridae | E1/E2/(E3) | yes | yes | h/a[‡] | Rubella |
| Flaviviridae | E | n.d. | yes | h/a | yellow fever |
| Rhabdoviridae | G | n.d. | yes | h/a | rabies |
| Orthomyxoviridae | HA | yes | yes | h/a | influenza |
| Bunyaviridae | G1/G2 | n.d. | yes | h/a | Korean hemorrhagic fever |
| Neutral pH Fusers | | | | | |
| Coronaviridae* | S | n.d. | n.d. | h/a | common colds |
| Paramyxoviridae | F | yes | (yes)[1] | h/a | Respiratory Syncytial virus, measles, mumps |
| Retroviridae[#] | env | yes | (yes)[1] | h/a | HIV |
| Hepadnaviridae | S | n.d. | n.d. | h/a | hepatitis B |
| Herpesviridae | gB, gD, gH | n.d. | n.d. | h/a | Herpes simplex, CMV, chicken pox |
| Poxviridae | 14 kD/n.d. | n.d. | n.d. | h/a | smallpox |

-continued

Families of Enveloped Viruses

| Virus Family | Fusion Protein | Fusion Peptide | Conf. Change | Host Species | Representative Disease States |
|---|---|---|---|---|---|
| others | | | | | |
| Classification Unknown | | | | | |
| Filoviridae | | | | h/a | Marburg virus |
| Arenaviridae | | | | h/a | Lassa fever |
| Iridoviridae | | | | a | African swine fever |

‡h = human; a = animal
*Some isolates of coronaviruses fuse at low pH
most retroviruses (e.g., HIV, HTLV) fuse at neutral pH, although one (MMTV) has been documented to fuse at low pH
[1]Not yet determined and confirmed.

In addition, several of the new compounds were tested and found to inhibit fusion mediated by the HIV-1 fusion protein. The $IC_{50}$ for compound 90 was 2 μM and for compound 107 was 50 μM. This shows that the new class of compounds are effective in general in inhibiting fusion mediated by a class of membrane fusion proteins and will be active for most, if not all, enveloped viruses listed above.

The present experiments also predict that the new class of compounds will be effective in treating viral infections in humans and other animals. Examining assays for amantadine activity and corresponding procedures in humans suggests that identifying specific treatment regimens using the new class of compounds to treat viral infections in humans, and even other animals, will be straightforward. See Goodman & Gilman, THE PHARMACOLOGICAL BASIS OF THERAPEUTICS, 7th Edition, Macmillan, (1985) at p. 1232.

In general, compounds of interest include the following structures

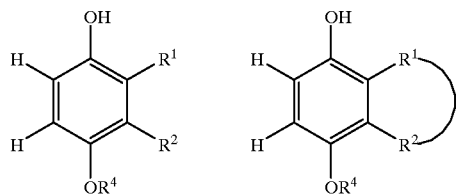

The compounds are 2-$R^1$, 3-$R^2$ derivatives of 1,4-hydroquinone ($R^4$=H) with a variety of $R^1$ and $R^2$ groups, and the corresponding tantomer. The oxidized, benzoquinone form of each derivative is generally active as well. The strongest inhibitors found to date are 1,4-hydroquinone derivatives with a single hydrophobic ring fused at the 2-3 bond or a hydrophobic substituent smaller than a phenyl ring at the 2 position. A related class of active compounds include one substituted diol, e.g. 4-$OR^4$ where $R^4$ is a saturated or unsaturated hydrocarbon of less than 4 carbons. A chart of the compounds tested, including those which were inactive, is presented below in Table 7. One key compound was 5,8-dihydro-5,8-methano-1,4-naphthalenediol, compound 83A:

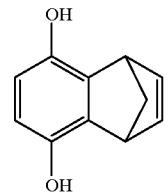

The two most active compounds tested were 3',6'-dihydroxybenzenenorbornane, compound 111 and tert-butylhydroquinone, compound 117:

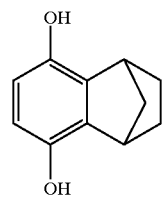

111

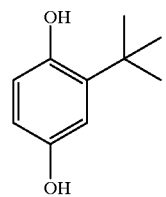

117

More generally, $R^1$ and $R^2$ each can be a hydrocarbon, saturated or unsaturated, potentially aromatic, generally hydrophobic, up to about $C_{10}$, but $R^1$ and $R^2$ taken together should include at least two carbon atoms. $R^1$ or $R^2$ or both can be electron donating or slightly electron withdrawing, e.g. —$CH_2$—O—$CH_3$, $CH_2$—O—$R^3$ (where $R^3$ is a generally hydrophobic hydrocarbon, saturated or unsaturated, potentially aromatic, up to about $C_{10}$) or —$CH_2$—COOH or esters thereof. $R^1$ and $R^2$ cannot both be strongly electron withdrawing, e.g. halogen or nitrile. $R^1$ and $R^2$ are preferably hydrophobic. $R^1$ and $R^2$ can be part of a carbocyclic structure, e.g. naphthoquinone or compound 83, but should not be part of a highly polar heterocycle. Such a carbocyclic structure may be saturated, unsaturated, or aromatic. Preferably $R^1$, and $R^2$ if present, should have a carbon residue in the position α- to the 1,4-dihydroquinone ring. Specific compounds that have shown significant activity are described in detail below.

Scintillation Proximity Assay

Figure 4:
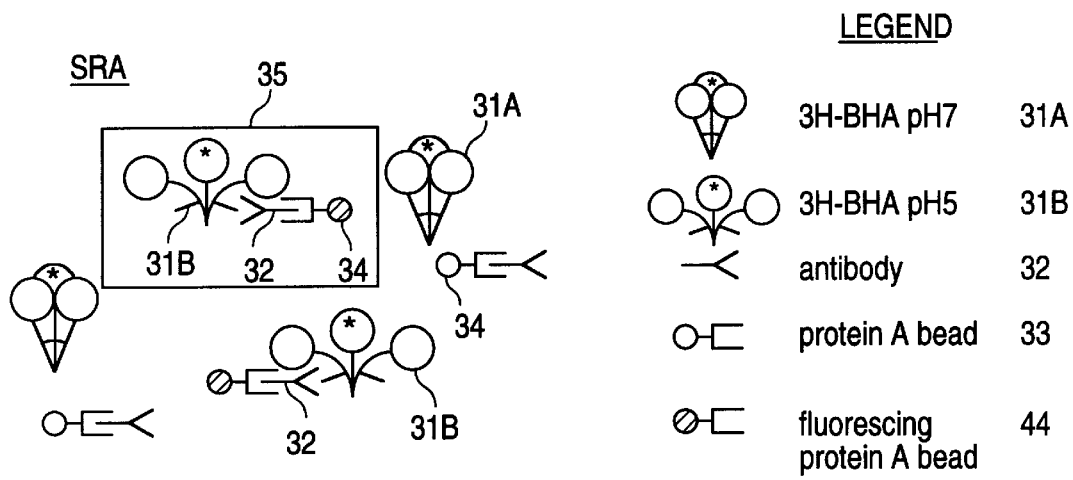
FIG. 4 illustrates the scintillation proximity assay (SPA).
Figure 5:
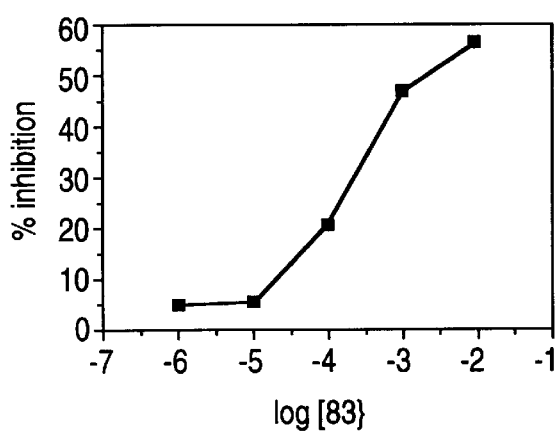
FIG. 5 illustrates the activity of compound 83 as a function of concentration.
Figure 6:
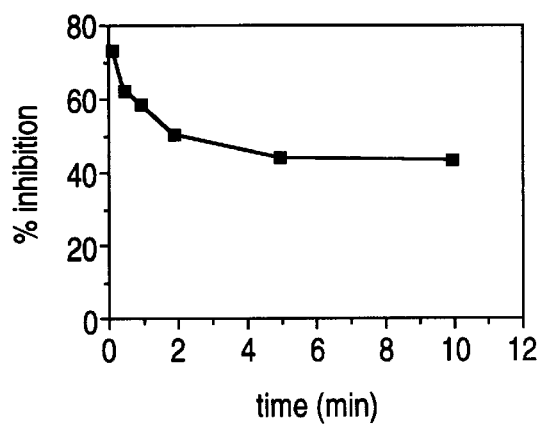
FIG. 6 illustrates inhibition by compound 83 as a function of time at low pH.

The primary assay used for screening compounds was the scintillation proximity assay (SPA). SPA recognizes the low pH form of hemagglutinin by its ability to bind conformation-specific antibodies. FIG. 4 shows the precipitation of low pH BHA with the fusion peptide antibody by the SPA technique. Detection of BHA-antibody complexes by SPA will be referred to as precipitation even though the complexes are not centrifugally pelleted. In a mixture of BHA in various conformations the fusion peptide antibody will specifically bind to hemagglutinin with exposed fusion peptides.

To differentiate neutral and low pH forms of BHA the SPA assay exploits the distance-dependent quenching of low energy β-emitters by aqueous media. Low pH trimers are more able to bind the fusion peptide antibody and thus are distinguished from trimers which remain in the neutral pH conformation, e.g. in the presence of inhibitor compounds. Referring to FIG. 4, primary fusion peptide antibody 32 is bound to both radiolabeled low pH BHA 31B and to protein A which is coupled to microspheres 34 containing scintillant. Only labeled BHA bound to antibody-scintillant-bead complexes 35 will trigger emission of light by the fluorophore. Energy produced by unbound protein 31A will be dissipated in the solvent and thus remain undetected.

The compounds being screened by SPA are present during scintillation counting. Some of the chemicals, particularly those that are highly colored, quench the detection of radioactivity. A control ("POST") distinguishes whether apparent inhibition arises from inhibition of the conformational change or from nonspecific effects. The test compound is added to a sample of BHA that had previously been acidified and reneutralized. The mixture is then precipitated as usual. Since the BHA treated in this manner is known to be in the low pH conformation, a reduction in measurable cpm compared to controls with ligand omitted proves the compound interferes with the detection system.

The commercial compounds selected from the FCD were screened by SPA using the fusion peptide antibody. The results are shown in Table 1. POST controls were carried out for compounds which reduced the cpm precipitated by at least 10%. Highly toxic compounds or compounds insoluble in DMSO or water were not tested.

TABLE 1

Effect of compound 83 (at 1 mM) in the SPA with the fusion peptide antibody.

| compound | % inhibition | sample % sd | POST |
|---|---|---|---|
| 83 | 49.1 ± 15.0 | 2.1 | 4.2 |

The activity of compound 83 could not be attributed to nonspecific quenching. To study the effect of compound 83 in more detail, the activity as a function of concentration was determined (FIG. 5). Half-maximal inhibition fell between $10^{-3}$ M (174 μ/ml) and $10^{-4}$ M (17.4 μg/ml).

Referring to FIG. 5, in testing the dose response of compound 83 in the SPA, the % inhibition is averaged over duplicate precipitations from 1–3 independent experiments. The mM point is the average of 16 independent determinations (Table 1). Values are corrected for nonspecific quenching. Inhibition of the POST controls was 26.4% at 10 mM and 4% or less at all other concentrations. Standard deviations are: 1 μM, 9.5; 10 μM, 19.6; 0.1 mM, 17.1; 1 mM, 15.0. These errors reflect the daily variability of the activity at each concentration.

Since compound 83 at concentrations below 10 mM does not reduce precipitation in POST controls, the observed inhibition is presumably due to an interaction with hemagglutinin. To distinguish whether the effect is a result of noncovalent binding or a covalent modification, a dilution experiment was carried out. If the activity is due to noncovalent binding it should be reversible by dilution; covalent modifications are less likely to be reversed under these conditions. Samples were preincubated with 1 mM 83. Sample 1 was maintained at $10^{-3}$ M throughout the experiment but sample 2 was diluted to $10^{-5}$ M, a concentration at which negligible inhibition had been observed. All samples were incubated at low pH for 5 minutes then precipitated by SPA with the fusion peptide antibody, as usual. In Table 2, "% inhibition" is the % reduction in cpm precipitated compared to controls with 83 omitted. POST controls showed no nonspecific quenching by 83 at these concentrations. The results reveal that the inhibition caused by compound 83 at 1 mM is reversible by dilution, suggesting that the interaction with BHA is noncovalent.

TABLE 2

SPA dilution experiment with compound 83.

| sample | conc (M) | % inhibition |
|---|---|---|
| 1 | $10^{-3} \rightarrow 10^{-3}$ | 45.3 |
| 2 | $10^{-3} \rightarrow 10^{-5}$ | 4.6 |

However, the dilution experiment does not rule out the possibility that compound 83 has an irreversible effect caused by acidification. To address this, inhibition as a function of time at low pH was determined. If the effect is due to chemical reactivity at pH 5, inhibition should remain constant or increase during extended incubations. If the effect of compound 83 is noncovalent in nature then, due to the irreversibility of the conformational change itself, the inhibition would be expected to decrease as a function of time. The results for 10 minutes of exposure to pH 5.0 are shown in FIG. 6. Initially, at 10 seconds, 73% inhibition is observed. After 10 minutes, inhibition has decreased to 43%. This implies that inhibition is reversible at low pH. Combined with the results of the dilution experiment, the data suggest that compound 83 is a reversible inhibitor.

There are interesting biological implications of this experiment. In order for the antiviral strategy to be successful, the inhibitors must prevent fusion in the acidic endocytic compartments until the virus is inactivated in the lysosome. For the WSN strain of influenza, the mean time from endocytosis to degradation of the hemagglutinin is approximately 20 minutes longer then the average time (~25 minutes) for endocytosed virions to encounter the pH threshold of fusion. As shown in FIG. 6 for C22 BHA, compound 83 still maintains 60% of its maximal inhibition of fusion peptide exposure even after 10 minutes of exposure to pH 5.0. This suggests that 83 or a stronger analog may be able to prevent fusion long enough to inhibit viral infection. Note that the antiviral compound does not necessarily have to prevent conformational changes along the entire endocytic pathway. It is possible that hemagglutinin reaching a prelysosomal compartment with a pH below the fusion threshold will undergo rearrangements that do not trigger membrane fusion.

Testing Derivatives of the Lead Compound

83K

83A

The chemical structure of 83 reveals the potential of the compound to tautomerize to an alternate form. The structures of the two isomers, 83K and 83A, are shown above. The commercially available 83 may be a mixture of the two forms. In order to determine which is the active species, the two compounds were prepared separately (see Experimental section) and tested individually. The precipitation of BHA in the presence of each of the two purified components as well as with the original commercial sample are compared in FIG. 7. Inhibition was observed with all three species. Reactions were carried out as described in the methods. Cpm precipitated are averaged from duplicate samples from a single experiment. The concentration profile of 83K exactly mimics that of 83, but compound 83A is active at 100-fold lower concentrations. Although this suggests that both compounds are active, it does not rule out the possibility that the activity observed with 83 and 83K is due to contamination by 83A, possibly generated during the course of the experiment.

The fortuitous increase in inhibitory activity observed with 83A suggested testing other analogs of 83. Compounds were found by substructure searching using MACCS-II/3D. Chemicals selected represent the commercially available variety of substituents. The structures of these compounds are shown in Table 7.

The derivatives were tested for their ability to inhibit fusion peptide exposure, as measured by SPA with the fusion peptide antibody. They span a range of activities, from inactive at mM concentrations to active in the $\mu$M range (Selected values in Table 3). Controls showed that none of the compounds tested (84, 89, 90, 91, 99, 116, 117, 118, 119, 121, and 135 at 1mM and 114 and 124 at 0.1 mM) affect the pH of the reactions. The approximate concentrations at which half-maximal inhibition was observed ($IC_{50}$) for each ligand are listed in Table 6.

TABLE 3

Activity of derivatives of compound 83 in the SPA with the fusion peptide antibody. "% inhibition" is the % reduction in cpm compared to controls without trial ligand. All precipitations were done in duplicate. For samples repeated in independent experiments the mean % inhibition, its standard deviation, and the number of experiments averaged (n) are reported. Results from POST controls were treated similarly.

| compound | pure | log conc (M) | sample % inhibition | n | POST control % inhibition | n |
|---|---|---|---|---|---|---|
| 83K | * | −3 | 59.5 ± 3.7 | 3 | −5.3 ± 2.1 | 2 |
|  |  | −4 | 6.6 ± 4.4 | 3 | 3.0 | 1 |
|  |  | −5 | 0.9 ± 4.2 | 3 | 0.8 ± 12.7 | 2 |
|  |  | −6 | −2.5 ± 2.1 | 3 | −6.2 | 1 |
| 83A | * | −3 | 54.3 ± 17.7 | 6 | 0.5 ± 1.1 | 2 |
|  |  | −4 | 48.6 ± 19.7 | 6 | −0.9 ± 1.5 | 2 |
|  |  | −5 | 18.7 ± 21.1 | 5 | −0.5 | 1 |
|  |  | −6 | 6.1 ± 9.1 | 4 | 10.8 | 1 |
| 90 | * | −3 | 86.4 | 1 | 68.2 | 1 |
|  |  | −4 | 47.7 | 1 | 30.8 | 1 |
|  |  | −5 | 4.3 | 1 | 4.6 | 1 |
|  |  | −6 | −3.8 | 1 | n.d. | 0 |
| 91 |  | −3 | 88.6 | 1 | 54.5 | 1 |
|  |  | −4 | 66.5 | 1 | n.d. | 0 |
|  |  | −5 | 61.7 | 1 | n.d. | 0 |
|  |  | −6 | 15.0 | 1 | n.d. | 0 |
| 111 | * | −3 | 65.7 ± 1.6 | 2 | 13.3 | 1 |
|  |  | −4 | 70.5 | 1 | 9.5 | 1 |
|  |  | −5 | 26.6 | 1 | n.d. | 0 |
|  |  | −6 | 8.0 | 1 | n.d. | 0 |
| 112 |  | −3 | 40.1 | 1 | n.d. | 0 |
| 117 | * | −3 | 79.3 ± 15.4 | 3 | −3.4 | 1 |
|  |  | −4 | 80.3 ± 1.5 | 2 | 2.9 | 1 |
|  |  | −5 | 46.4 ± 21.8 | 2 | 9.1 | 1 |
|  |  | −6 | −0.1 ± 18.7 | 2 | 4.7 | 1 |

"n.d." not done.
Stock solutions of all compounds were prepared in DMSO.

Compounds 93, 113 and 123 were insoluble in DMSO and were not tested. Compounds 101, 102, 105, 106, 107, and 110 were only partially soluble at 1 mM. '*' indicates compounds known to be pure (see Experimental section). Impure compounds 91, 97 and 125 and unstable 110 were not pursued. Data could not be obtained for higher concentrations of 114 due to complete quenching of the samples.

Averaged over 5 independent experiments, the maximum inhibition for nonquenching compounds was 65.6±7.8%. No compound was able to reduce the cpm precipitated to background levels. The inhibitory activity could not be increased by raising the concentration of ligand (see for example 83A, 111, and 117 in Table 3), and the maximum observed inhibition was similar for sufficiently potent compounds. Since the BHA was>90% pure and no counts were precipitated without prior acidification, the residual 34% is not due to precipitation of a radiolabeled contaminant. There are several possible explanations for the lack of complete inhibition. The compounds may only be 66% effective at inhibiting the conformational change due to weak interactions with the protein. The compounds may be binding to a site unable to regulate fusion peptide exposure completely. If 100% inhibition requires interactions with 2 or more sites per trimer, the compounds may not be binding to a sufficient number of sites concurrently. Alternatively, a fraction of the BHA trimers may be misfolded or otherwise uninhibitable.

Hemagglutination

Compounds inhibiting the conformational change of hemagglutinin were tested for their ability to inhibit fusion and infectivity. Assays measuring these processes depend on viral recognition of cellular receptors. To rule out the possibility that any observed inhibition in these experiments is due to inhibition of virus-cell binding, hemagglutination tests were performed with some of the compounds. Derivatives 83 (1 mM), 91 (1 mM), 97 (0.1 mM), 110 (1 mM), and 117 (10 μM) clearly had no effect on binding between intact virions and their receptors on red blood cell membranes.

Hemolysis

The results from the SPA experiments suggest that compound 83 and several derivatives can inhibit exposure of the fusion peptide. If so, they should also inhibit fusion. The hemolysis assay has been used previously to study the membrane fusion activity of hemagglutinin. Influenza viruses rupture the membranes of red blood cells under fusion-inducing conditions. The amount of hemoglobin released, as measured by the absorbance at 570 nm, is proportional to the amount of fusion. Therefore, compounds capable of preventing hemagglutinin-mediated fusion should reduce the OD by an amount related to the inhibitory activity.

There are two potential problems with using the hemolysis assay to screen compounds. 1) Some compounds can lyse red blood cells (rbcs), even in the absence of virus. Control samples in which rbcs were incubated with compounds under the conditions of the hemolysis experiment revealed the extent of compound-induced lysis. The OD of these control samples was then subtracted from the OD of samples containing virus plus compound. 2) The compounds may alter the absorption spectrum of hemoglobin. The ability of the compounds to "quench" the $OD_{570}$ of hemoglobin was measured by the "Hb" control. These control samples were identical to the hemolysis samples except that a solution of hemoglobin was used in place of intact rbcs. The reduction in $OD_{570}$ caused by each compound in the Hb control is listed in Table 4. The Hb control was a reliable way of identifying compounds causing a complete loss of OD due to redox activity (101, 107) but could not always be used to quantitate the percent reduction in OD due to inhibition of fusion.

The results of screening selected derivatives of 83 by hemolysis are shown in Table 4 and summarized in Table 6. The % reduction in $OD_{570}$ of each sample compared to the appropriate DMSO-containing control is given for both hemolysis reactions and Hb controls (see text). Rbcs used in the Hb control for 117 were prelysed in NP40 detergent solution. OD values are averaged over n independent experiments. "n.d.", not done. '*' indicates a pure or purified compound. Hemolysis Protocol 3 was used. Compounds 83, 91, 97, 117, and 126 apparently inhibited hemolytic activity while 99, 116, 120, and 135 did not. The concentration profiles are in good agreement with those observed by SPA. These data suggest that certain derivatives of 83 are able to inhibit hemagglutinin-mediated hemolysis.

TABLE 4

Hemolysis assay results

| compound | pure | log conc (M) | hemolysis % ↓ OD | n | Hb control % ↓ OD | n |
|---|---|---|---|---|---|---|
| 83 | | −3 | 67.0 ± 15.1 | 4 | 16.5 ± 2.1 | 2 |
| | | −4 | 17.9 ± 20.0 | 2 | n.d. | 0 |
| | | −5 | 11.3 ± 10.3 | 2 | n.d. | 0 |
| 90 | * | −3 | 90.3 | 1 | 68.1 | 1 |
| | | −4 | 33.1 | 1 | 57.1 | 1 |

TABLE 4-continued

Hemolysis assay results

| compound | pure | log conc (M) | hemolysis % ↓ OD | n | Hb control % ↓ OD | n |
|---|---|---|---|---|---|---|
| | | −5 | 4.7 | 1 | 24.9 | 1 |
| 91 | | −3 | 91.0 ± 14.6 | 4 | 29.6 ± 2.5 | 3 |
| | | −4 | 60.5 ± 0.7 | 2 | 26.8 ± 5.0 | 4 |
| | | −5 | 13.2 | 1 | 11 | 1 |
| | | −6 | −5.1 | 1 | 3 | 1 |
| 97 | | −3 | 102.0 ± 5.8 | 4 | 55.0 ± 13.3 | 3 |
| | | −4 | 94.6 | 1 | 37.6 ± 4.9 | 2 |
| | | −5 | 23.7 | 1 | 31 | 1 |
| | | −6 | 6.6 | 1 | 13.0 | 1 |
| 99 | * | −3 | 28.7 | 1 | 27.8 | 1 |
| 101 | | −3 | 112.2 | 1 | 93.0 | 1 |
| 107 | | −3 | 104.1 | 1 | 92.5 | 1 |
| 111 | * | −3 | 36.7 ± 0.6 | 2 | 64.9 ± 0.5 | 2 |
| | | −4 | −6.9 ± 9.3 | 2 | 40.4 ± 1.3 | 2 |
| 116 | * | −3 | 17.3 | 1 | 44.0 | 1 |
| | | −4 | 7.7 | 1 | 31.6 | 1 |
| 117 | * | −3 | 116.0 | 1 | 17.8 | 1 |
| | | −4 | 31.6 ± 6.9 | 2 | 9.9 ± 2.8 | 2 |
| | | −5 | 13.9 | 1 | 7.9 | 1 |
| 120 | * | −4 | 6.2 | 1 | 4.4 | 1 |
| 121 | * | −3 | 116.2 | 1 | 68.0 | 1 |
| | | −4 | 31.5 ± 7.8 | 2 | n.d. | 0 |
| | | −5 | −4.6 ± 0.1 | 2 | n.d. | 0 |
| 126 | * | −3 | 101.4 ± 7.6 | 2 | 54.4 ± 3.7 | 2 |
| 135 | * | −3 | 80.3 | 1 | 75.2 | 1 |

FIG. 8 shows hemolysis with compound 91 at 0.1 mM as a function of pH. Maximum inhibition (61.0%) was observed at pH 5.0 and is consistent with the data in Table 4. This sample of 91 was subsequently shown to be impure but a similar pH effect is expected in each of the new compounds. FIG. 8 also reveals that compound 91 shifts the pH profile of hemolysis by approximately −0.2 pH units. Hemolysis Protocol 3 is described in the methods. The $OD_{570}$ of control samples at pH 5.0 and pH 7.0 were taken as 100% and 0%, respectively. Inhibition was not measured below pH 5.0 since hemolysis in control samples at lower pHs is reduced by an unknown mechanism.

Fusion from Without (Syncytia)

The ability of the compounds to inhibit fusion was also assessed by a third assay. "Fusion from without" measures the ability of viruses bound to cells to mediate syncytia formation. Nontoxic compounds were identified by the NMT viability assay as described below. However, to minimize misinterpretation of the results, only compounds which did not visibly affect the morphology of the cells were screened by this assay. Significant inhibition was not observed with compound 120 at 10 μM or 117 at 1 μM. In contrast, 117 at 10 μM completely abolished the ability of the virus to induce syncytia. These results are consistent with those from the SPA.

Infectivity

In theory, compounds which inhibit the conformational change and fusion should also prevent viral infectivity. The ELISA-based assay described below (EIA antiviral assay) was used to measure antiviral activity. Cell viability was measured in parallel to distinguish inhibition of viral replication from toxicity. Table 5 compares the effects of the compounds in the infectivity and MTT viability assays. While some of the compounds were toxic at the concentrations tested, others were able to inhibit viral replication under conditions at which the cells were viable. $IC_{50}$s, computed by the method described below, are listed in Table 6.

Experimental protocols and calculation of % inhibition are described below. All samples were done in triplicate in each experiment. The number of experiments averaged, n, is listed with the mean inhibition and standard deviation. Untested compounds ("n.d.") are completely toxic at concentrations at which specific inhibition is expected. '*' indicates a purified ligand.

TABLE 5

Effect of the analogs of compound 83 on infectivity and cell viability.

| compd | pure | log conc (M) | infectivity % inhibition | n | viability % inhibition | n |
|---|---|---|---|---|---|---|
| 83 | | −3 | 51.1 ± 28.3 | 2 | 92.9 ± 7.4 | 4 |
| | | −4 | 33.1 ± 20.2 | 2 | 46.4 ± 15.1 | 4 |
| | | −5 | 8.7 ± 6.7 | 2 | 7.3 ± 8.9 | 4 |
| | | −6 | 12.3 ± 2.5 | 2 | 3.4 ± 10.5 | 3 |
| 90 | * | −4 | 96.9 | 1 | 96.8 ± 3.8 | 2 |
| | | −5 | 81.7 ± 2.2 | 2 | 33.0 ± 9.9 | 2 |
| | | −6 | −3.3 ± 2.4 | 2 | −6.7 ± 7.3 | 2 |
| 91 | | −4 | 70.9 ± 39.8 | 2 | −4.3 ± 7.0 | 5 |
| | | −5 | 6.5 ± 7.0 | 5 | −2.0 ± 9.4 | 5 |
| | | −6 | −1.3 ± 4.0 | 2 | −0.06 ± 5.1 | 5 |
| 97 | | −4 | n.d. | 0 | 95.9 ± 8.0 | 4 |
| | | −5 | 92.6 ± 12.7 | 2 | 32.9 ± 30.9 | 9 |
| | | −6 | −4.7 ± 9.4 | 2 | −3.1 ± 7.9 | 9 |
| 99 | * | −4 | 113.7 ± 12.0 | 2 | 99.4 ± 0.4 | 2 |
| | | −5 | 35.9 ± 5.2 | 2 | −10.1 ± 10.0 | 2 |
| | | −6 | 26.2 ± 8.6 | 2 | −4.2 ± 9.0 | 2 |
| 101 | | −4 | n.d. | 0 | 97.4 | 1 |
| 105 | | −4 | n.d. | 0 | 100.5 | 1 |
| 107 | | −4 | n.d. | 0 | 96.9 | 1 |
| 110 | | −3 | 101.9 | 1 | 96.9 ± 0.4 | 2 |
| | | −4 | 91.9 ± 11.5 | 2 | 98.3 ± 1.2 | 6 |
| | | −5 | 61.1 ± 50.8 | 8 | 19.2 ± 15.6 | 8 |
| | | −6 | −9.8 ± 0.6 | 2 | 5.0 ± 12.5 | 7 |
| 111 | * | −4 | 102.4 ± 10.6 | 2 | 41.0 ± 17.0 | 2 |
| | | −5 | 57.4 ± 25.2 | 2 | −1.6 ± 0.8 | 2 |
| | | −6 | 21.7 ± 4.9 | 2 | 1.0 ± 5.8 | 2 |
| 114 | * | −4 | n.d. | 0 | 102.2 | 1 |
| | | −5 | 92.3 ± 12.7 | 2 | 53.7 ± 2.1 | 2 |
| | | −6 | 0.2 ± 0.2 | 2 | −4.3 ± 3.3 | 2 |
| 116 | * | −4 | 78.1 ± 10.0 | 2 | −23.6 ± 5.0 | 2 |
| | | −5 | 42.8 ± 4.7 | 2 | −9.4 ± 5.0 | 2 |
| | | −6 | 18.8 ± 1.7 | 2 | 3.6 ± 4.5 | 2 |
| 117 | * | −4 | 53.7 ± 26.4 | 2 | −26.1 ± 3.3 | 2 |
| | | −5 | 22.2 ± 13.2 | 2 | −13.7 ± 2.8 | 2 |
| | | −6 | 7.5 ± 0.1 | 2 | −8.4 ± 7.6 | 2 |
| 119 | | −4 | n.d. | 0 | 97.8 | 1 |
| 120 | * | −4 | −2.3 ± 3.1 | 2 | −7.0 ± 4.4 | 2 |
| | | −5 | 4.7 ± 0.9 | 2 | −6.0 ± 5.0 | 2 |
| | | −6 | 7.1 ± 6.7 | 2 | 0.5 ± 0.3 | 2 |
| 121 | | −4 | n.d. | 0 | 100.3 | 1 |
| 124 | | −4 | n.d. | 0 | 80.5 | 1 |
| 126 | * | −4 | 35.6 ± 0.6 | 2 | −7.6 ± 7.3 | 2 |
| | | −5 | 7.4 ± 1.8 | 2 | −9.2 ± 0.6 | 2 |
| | | −6 | 3.8 ± 5.5 | 2 | −6.9 ± 4.0 | 2 |

Summary of Experimental Results

Table 6 compares the results of screening compound 83 and its derivatives in conformational change, hemolysis, syncytia, and infectivity assays. Due to nonspecific effects, measurement of inhibition of fusion or infectivity was impossible for a number of the compounds. The available data show that compounds which inhibited the SPA also inhibited hemolysis, fusion from without, and infectivity. Conversely, compounds which did not inhibit the SPA did not inhibit hemolysis, fusion from without, or infectivity, except for compound 116 which was inactive in the SPA but inhibited infectivity.

Among the active compounds, there is generally good agreement between the concentration profiles in each assay. Results from compounds 90, 111, and 117 show that hemolysis consistently required somewhat higher concentrations to achieve 50% inhibition. Although hemolysis, syncytia formation, and infectivity can be inhibited in many ways, the coincidence of the observed concentration profiles with those from SPA analysis suggests that at least part of the observed inhibition has a common mechanism. Mounting evidence supports the idea that the interactions causing inhibition are specific for hemagglutinin and not proteins in general. The compounds do not abolish the binding capacity of antibodies, protein A, or the viral receptor on rbcs, they are not lethal to cells at all active concentrations, and they do not inhibit proteinase K (not shown) or HIV-1 protease. Combined with the observed reversibility, the data imply that the compounds are exerting a noncovalent effect on hemagglutinin resulting in inhibition of the fusion-inducing conformational change.

The two most active compounds, 111 and 117, are structurally related. Comparison of the structures of these compounds with less active or inactive compounds suggests which structural features improve activity and which reduce inhibition.

TABLE 6

Summary and comparison of results from the scintillation proximity, hemolysis, syncytia, and infectivity assays.

| | | $IC_{50}$ | | | |
|---|---|---|---|---|---|
| compound | pure | SPA | hemolysis | syncytia | infectivity |
| 83K | * | $10^{-3}$–$10^{-4}$ | $10^{-3}$–$10^{-4}$ | n.d. | toxic |
| 83A | * | $10^{-4}$–$10^{-5}$ | —† | n.d. | —† |
| 84 | | $10^{-3}$ | n.d. | n.d. | n.d. |
| 90 | * | $10^{-3}$–$10^{-4}$ | $10^{-3}$ | morph | $10^{-5}$ |
| 99 | * | $>10^{-3}$ | $>10^{-3}$ | toxic | $>10^{-5}$ |
| 105 | | $\geq 10^{-3}$–$10^{-4}$ | n.d. | n.d. | toxic |
| 107 | | $>10^{-3}$–$10^{-4}$ | quench | n.d. | toxic |
| 111 | * | $10^{-5}$ | $10^{-3}$–$10^{-4}$ | morph | $10^{-5}$ |
| 112 | | $\geq 10^{-3}$–$10^{-4}$ | n.d. | n.d. | n.d. |
| 114 | * | $>10^{-5}$ | n.d. | toxic | toxic |
| 115 | | $>10^{-3}$–$10^{-4}$ | n.d. | n.d. | n.d. |
| 116 | | $>10^{-3}$ | $>10^{-3}$ | morph | $10^{-4}$–$10^{-5}$ |
| 117 | * | $10^{-5}$–$10^{-6}$ | $10^{-4}$ | $10^{-5}$–$10^{-6}$ | $10^{-4}$–$10^{-5}$ |
| 120 | * | $>10^{-3}$ | $>10^{-4}$ | $>10^{-5}$ | $>10^{-3}$ |
| 121 | * | $>10^{-3}$ | $\geq 10^{-3}$ | n.d. | toxic |
| 124 | | $>10^{-3}$ | n.d. | n.d. | toxic |
| 126 | * | $10^{-3}$ | $10^{-3}$ | n.d. | $>10^{-4}$ |
| 135 | * | $>10^{-3}$ | $>10^{-3}$ | n.d. | n.d. |

† Compound 83A was initially active in the SPA assay but lost activity as it aged.
No active sample was available for testing in the other assays.

† Compound 83A was initially active in the SPA assay but lost activity as it aged. No active sample was available for testing in the other assays.

The midpoint of the dose response curves for each compound in each experiment is shown. Inhibitory activity has been corrected for nonspecific effects (quenching in SPA, hemoglobin oxidation in hemolysis, and cell toxicity in infectivity) as described below. A range of concentrations indicates that the $IC_{50}$ fell between two tested concentrations. For example, "$10^{-3}$–$10^{-4}$" implies that over 50% inhibition was observed at 1 mM but less than 50% inhibition was observed at 0.1 nM. "$>10^{-3}$" indicates that 50% inhibition was not achieved at 1 mM, the highest concentration tested. Data for compounds without POST controls in the SPA (represented by $\geq$) are included as an upper bound on the activity of the sample. "quench" means that inhibitory activity could not be assessed due to quenching by the compound. "toxic" represents compounds determined to be toxic to the cells used in the assay. "morph", the compound altered the morphology of the cells. "n.d.", not done. '*' indicates a purified compound. 91, 97, 125 are impure, 110 is unstable, and 93, 113, 123 are insoluble in DMSO. Compounds 85, 86, 87, 88, 89, 92, 94, 95, 96, 98, 100, 101, 102, 103, 104, 106, 108, 109, 118, 119, 122, and 127 showed no inhibition in the SPA assay at 1 μM–1 mM. Note that hemagglutinin is exposed to low pH for 5 minutes in the SPA and syncytia assays but for 15 minutes in hemolysis.

Cells, Viruses, Antibodies, and Reagents

Wt-HA-expressing CHO-DUKX cells (Wtm8005 cell line), a gift of Dr. Don Wiley, were maintained in G418 media (MEM-alpha (minimal essential media alpha) without nucleosides, 10% supplemented bovine calf serum (SCS), 2 mM glutamine, 100 U/ml penicillin, 100 mg/ml streptomycin, 600 μg/ml geneticin (Gibco BRL), 0.3 μM methotrexate). CV-1 cells (American Type Tissue Culture) were maintained in CV-1 growth media (DME (Dulbecco MEM), 10% SCS, 2 mM glutamine, 100 U/ml penicillin, 100 mg/ml streptomycin). MDCK2 (Madin-Darby canine kidney) cells, gifts of Dr. Barry Gumbiner, were grown in MDCK growth media (MEM-EBSS (MEM with Earle's balanced salt solution), 5% SCS, 2 mM glutamine, 100 U/ml penicillin, 100 mg/ml streptomycin, 25 mM HEPES (N-2-hydroxyethylpiperazine-N'-2-ethanesulfonic acid) pH 7.2). Unless otherwise noted, all tissue culture reagents were obtained from the UCSF Cell Culture Facility.

Inoculum for X31 influenza virus (H3N2) and its plaque purified subtype C22 were the gift of Dr. Ari Helenius. Doms, R. W., Gething, M. -J., Henneberry, J., White, J. and Helenius, A., "Variant influenza virus hemagglutinin that induces fusion at elevated pH," *J. Virol.* 57: 603–13 (1986).

Drs. Richard Lerner and Ian Wilson of Scripps provided some of the fusion peptide antiserum. These anti-peptide antibodies were raised against residues 1–29 of HA2. The site A mouse monoclonal antibody was the gift of Dr. John Skehel.

Acquisition and Dissolution of Trial Inhibitors

Sources for all commercial and synthesized compounds are listed in Table 7. Synthesis, purification, and characterization of selected compounds are summarized below. Stock solutions were prepared fresh daily. All solutions of the test compounds were prepared in dimethyl-sulfoxide (DMSO). Compounds insoluble in DMSO at sufficiently high concentrations were not tested.

TABLE 7

Commercial and synthesized derivatives of 83

| ID | name | source | FW | structure |
|---|---|---|---|---|
| 83A | 5,8-dihydro-5,8-methano-1,4-naphthalenediol | SERES | 174 | 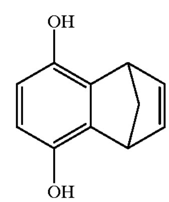 |

| | 83A | 83K |
|---|---|---|
| SPA | 4–5 | 3–4 |
| HEM | — | 3–4 |
| INF | — | toxic |

| 84 | 2,6,6-trimethyl-2-cyclohexene-1,4-dione | Fluka | 152 | |
| SPA | 3 | | | |
| HEM | | | | |
| INF | | | | |

| 85 | dimethylbicyclo[2.2.1]-5-heptene-2,3-dicarboxylate (inactive) | Lancaster Synthesis | 210 | |

| 86 | 3,6-endoxo-1,2,3,6-tetrahydrophthalic acid (inactive) | Tokyo Kasei | 184 | |

TABLE 7-continued

Commercial and synthesized derivatives of 83

| ID | name | source | FW | structure |
|---|---|---|---|---|
| 87 | 5-norbornene-2,3-dicarboxylic acid monomethyl ester (inactive) | TCI | 196 | 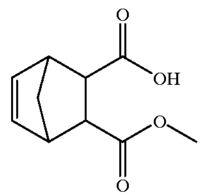 |
| 88 | 1,2,3,4,4A,5,8,8A-octahydro-1,4:5,8-dimethanonaphth-2-yl acetate (inactive) | Bader | 218 | 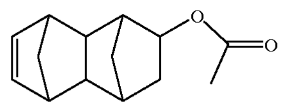 |
| 89 | cis-5-norbornene-endo-2,3-dicarboxylic acid (inactive) | Aldrich | 182 | 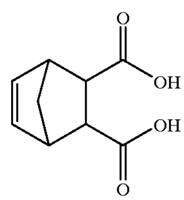 |
| 90 | 1,4-naphthoquinone<br>SPA 3–4<br>HEM 3<br>INF 5 | Aldrich | 158 | 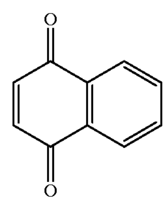 |
| 91 | 5,8-dioxo-1,4,4A,5,8,8A-hexahydro-1-naphthalene carboxylic acid (preliminary results):<br>SPA 4<br>HEM 3–4<br>INF 4–5 | Bader | 206 | 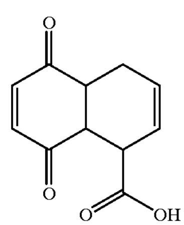 |
| 92 | 5,5-dichlorotetracyclo-[6.2.1.0,2,7.0.4.6] undec-9-ene (inactive) | Bader | 215 | 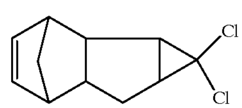 |
| 93 | 1,4,4A,4B,5,8,8A,8B,9,10-decahydro-1,4:5,8-dimethanoanthracene-9,10-dione (insoluble) | Bader | 240 | 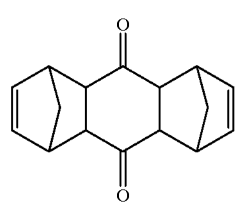 |
| 94 | N-hydroxy-5-norbornene-2,3-dicarboximide (inactive) | Aldrich | 179 | 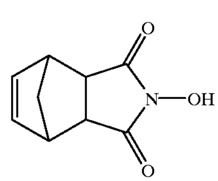 |

TABLE 7-continued

Commercial and synthesized derivatives of 83

| ID | name | source | FW | structure |
|---|---|---|---|---|
| 95 | N-methyl-5-norbornene-2,3-dicarboximide (inactive) | Bader | 177 | 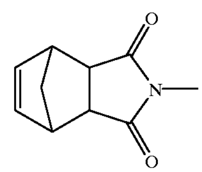 |
| 96 | 1,2,3,4,4A,5,8,8A-octahydro-1,4:5,8-dimethano-2-naphthol (inactive) | Bader | 176 | 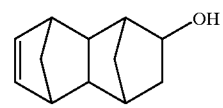 |
| 97 | methyl 5,8-dioxo-1,4,4A,5,8,8A-hexahydro-1-naphthalenecarboxylate (preliminary results): | Bader | 220 | 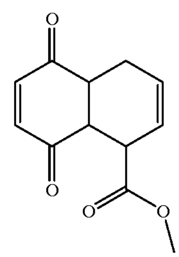 |
| SPA | 5 | | | |
| HEM | 4 | | | |
| INF | 5–6 | | | |
| 98 | 3-(N-phenylcarbamoyl)-5-norbornen-2-carboxylic acid (inactive) | Bader | 257 | 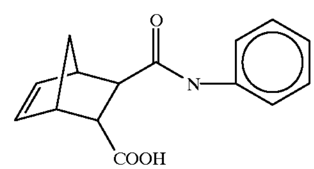 |
| 99 | 2,3-dimethylhydroquinone | Aldrich | 138 | 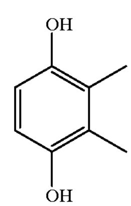 |
| SPA | <3 | | | |
| HEM | <3 | | | |
| INF | <5 | | | |
| 100 | phthalimide (inactive) | Aldrich | 147 | 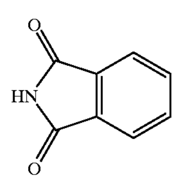 |
| 101 | 4-chloro-1-naphthol (inactive) | Aldrich | 179 | 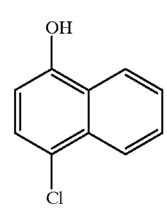 |

TABLE 7-continued
Commercial and synthesized derivatives of 83
| ID | name | source | FW | structure |
|---|---|---|---|---|
| 102 | quinizarin (inactive) | Aldrich | 240 | 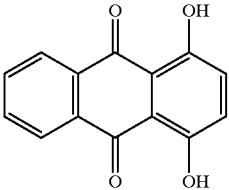 |
| 103 | 2,3-dicyanohydroquinone (inactive) | Aldrich | 160 | 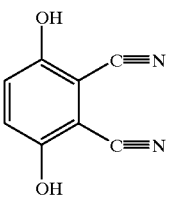 |
| 104 | hydroquinone (inactive) | Aldrich | 110 | 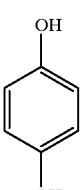 |
| 105 SPA <3–4 HEM — INF toxic | phenylhydroquinone | Aldrich | 186 | 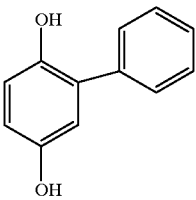 |
| 106 | 1-naphthol (inactive) | Aldrich | 144 | 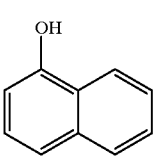 |
| 107 SPA ≦3–4 HEM quench INF toxic | 4-methoxy-1-naphthol | Aldrich | 174 | 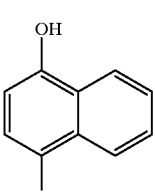 |
| 108 | phthalhydrazide (inactive) | Aldrich | 162 | 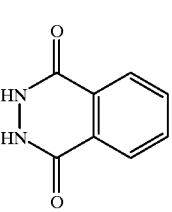 |

TABLE 7-continued

Commercial and synthesized derivatives of 83

| ID | name | source | FW | structure |
|---|---|---|---|---|
| 109 | hydroxydicyclopentadiene (inactive) | TCI | 150 | |
| 110 | 1,4-dihydroxynaphthalene (unstable - air oxidizes to compound 90) | TCI | 160 | |
| 111<br>SPA 5<br>HEM 3–4<br>INF 5 | 3',6'-dihydroxybenzonorbornane | TCI | 176 | |
| 112<br>SPA ≦3–4<br>HEM<br>INF | 2-(2,5-dihydroxyphenyl)-2-thiopseudourea hydrochloride | Bader | 221 | |
| 113 | xanthine 3-N-oxide (insoluble) | Sigma | 168 | |
| 114<br>SPA <5<br>HEM —<br>INF toxic | 1,4-anthraquinone | Lancaster Synthesis | 208 | |
| 115<br>SPA <3–4<br>HEM —<br>INF — | methyl 2,5-dihydroxybenzoate | Frinton Labs | 168 | |

TABLE 7-continued

Commercial and synthesized derivatives of 83

| ID | name | source | FW | structure |
|---|---|---|---|---|
| 116 | 2,5-dimethylhydroquinone | Pfaltz & Bauer | 138 | |
| SPA | <3 | | | |
| HEM | <3 | | | |
| INF | 4–5 | | | |
| 117 | tert-butylhydroquinone | Aldrich | 166 | |
| SPA | 5–6 | | | |
| HEM | 4 | | | |
| INF | 4–5 | | | |
| 118 | 2-methyl-1,4-naphthoquinone (inactive) | Aldrich | 172 | |
| 119 | 5-hydroxy-1,4-naphthoquinone (inactive) | Aldrich | 174 | |
| 120 | 2-hydroxy-1,4-naphthoquinone | Aldrich | 174 | |
| SPA | <3 | | | |
| HEM | <4 | | | |
| INF | <3 | | | |
| 121 | 4-amino-1-naphthol hydrochloride | Aldrich | 196 | |
| SPA | <3 | | | |
| HEM | ≦3 | | | |
| INF | toxic | | | |
| 122 | ethyl 2,4-dihydroxy-6-methylbenzoate (inactive) | Aldrich | 196 | |

TABLE 7-continued

Commercial and synthesized derivatives of 83

| ID | name | source | FW | structure |
|---|---|---|---|---|
| 123 | vitamin K1 (insoluble) | Aldrich | 451 | 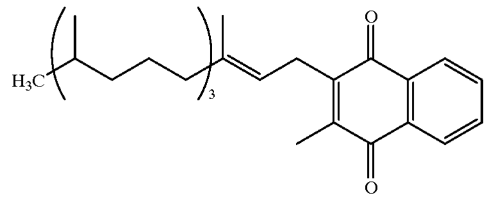 |
| 124 SPA HEM INF | 1,2-dihydroxynaphthalene <3 — toxic | Aldrich | 160 | |
| 125 SPA HEM INF | 1-amino-5-naphthol (preliminary results): 4–5 — — | Pfaltz & Bauer | 196 | |
| 126 SPA HEM INF | 1,5-naphthalenediol 3 3 <4 | Aldrich | 160 | |
| 127 | 8-hydroxyquinoline (inactive) | Baker | 147 | 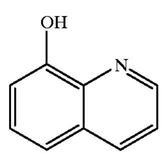 |
| 135 | 2-bromo-1,4-naphthoquinone | SERES | 237 | 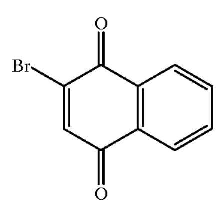 |

For convenience, the results of the inhibition assays for are summarized in Table 7 as well. The data presented in Table 6 for the scintillation proximity assay (SPA), hemolysis (HEM), and infectivity (INF) assays are summarized in Table 7, listing the negative log of each $IC_{50}$ in Table 6. Thus, a larger number indicates increased inhibitory activity. Note that compound 83K showed some activity, but 83A was more active in the SPA assay.

Preparation of Viral Inoculum

C22 influenza was propagated in chicken embryos as previously described. Skehel, J. J. and Schild, G. C., "The polypeptide composition of influenza A viruses," *Virology* 44: 396–408 (1971). Ten day old fertilized eggs were infected with 0.01 hemagglutinating units (HAU) of virus in 0.1 cc sterile PBS. Infection proceeded for two days at 37° C. After incubation overnight at 4° C., the allantoic fluid was harvested sterilely then cleared of debris by centrifugation for 5 minutes at 700×g (2000 rpm in a Beckman Accuspin).

Virus Purification

Virus was purified from inoculum as previously described. Skehel, J. J. et al., loc. cit. Fertilized eggs were infected as above. Following a 30 minute debris spin, the virus was pelleted at 40,000×g (Type 19 rotor at 17K rpm) for 2 hours 40 minutes. Pellets were eluted overnight in PBS then dounced. The slurry was incubated at 37° C. for 15–30 minutes, then spun for 5 minutes at 1000×g (2500 rpm in a Beckman Accuspin) to pellet red blood cells and aggregates. The virus was layered over a 30%/60% w/vol sucrose/PBS step gradient and spun at 75,000×g (SW27, 24K rpm) for 90 minutes. The interface band was collected and pelleted in PBS under the same conditions. Pellets were eluted overnight at 4° C. then dounced. Aggregates were cleared as above. Yield of viral protein was determined by Lowry assay.

Purification of Unlabeled BHA

Bromelain-digested hemagglutinin trimers were isolated from influenza virions following a published procedure. Doms, R. W., Helenius, A. and White, J., "Membrane fusion activity of the influenza virus hemagglutinin: the low pH-induced conformational change," *J. Biol. Chem.* 260: 2973–81 (1985). Approximately 10 mgs purified virus were diluted to 5 mg/ml in 0.1 M Tris HCl, pH 8.0 then incubated overnight at 37° C. with 1.25 mg/ml bromelain (Sigma) and 50 mM β-mercaptoethanol (Biorad). Bromelain was inactivated by the addition of 1 mM N-ethylmaleimide (Sigma). The viral cores were pelleted at 4° C. in 0.1 M Tris at 100,000×g (SW41, 25K rpm) for 1 hour. The supernatant was concentrated then loaded on a 5%–25% w/vol sucrose/PBS gradient and centrifuged at 4° C. for 16 hr at 160,000×g (SW41, 37K rpm). Approximately 25 fractions were collected, and protein was detected by the Biorad procedure. Peak fractions corresponding to 9S trimers were pooled.

Purification of $^3$H-Leu-BRA

Metabolically labeled $^3$H-Leu-BHA was prepared similarly to $^{35}$S-Met-HA. Leu-media (MEM (GIBCO), 2.2 g/l NaHCO$_3$, 58 mg/l lysine, 15 mg/l methionine, pH 7.3) was used in place of Met- media and infected cells were labeled with 0.5 mCi/flask 3,4,5-$^3$H-leucine (NEN). The trypsin digestion was replaced by cleavage with 0.1 mg/ml bromelain, 20 mM β-mercaptoethanol for 16 hours at RT. The reaction was quenched by addition of 1 mM N-ethylmaleimide and BHA was purified by ricin affinity chromatography and sucrose gradient purification as above.

Scintillation Proximity Assay (SPA)

$^3$H-Leu BHA was diluted to 10,000 cpm (counts per minute) per 200 µl in MSSH buffer (10 mM HEPES, 10 mM MES, 10 mM succinate, 0.10 M NaCl, pH 7.0) containing 0.1% NP40. Protein was incubated with the specified concentration of trial compound for 25 minutes at RT. The same volume of solvent used to dissolve the compound was added to control samples and the final concentration of DMSO in all solutions was 0.67% v/v. A predetermined amount of 1N HAc was added to bring the reactions to the appropriate pH (usually pH 5.0). Following a 5 minute (unless specified otherwise) incubation at RT, reactions were reneutralized with 1N NaOH. For POST controls, compounds were added to the appropriate concentration after reneutralization. 200 µL aliquots of the protein solution were added to scintillation vials containing 100 µl protein A-SPA beads (Amersham), 5% fetal bovine serum (FBS), and antibody. Vials were incubated overnight at RT with constant shaking. Each reaction used 10 µl of fusion peptide antiserum diluted 1:10 with 50% glycerol. Cpm were detected in a Beckman LS3801 scintillation counter without addition of liquid scintillant.

Dilution Experiment $^3$H-Leu BHA at 1000 cpm/µl in MES Saline/0.1% NP40 was incubated with 1 mM compound 83 in DMSO or DMSO alone. The concentration of DMSO was 2.2% v/v. After incubation for 2 hours at RT, the samples were diluted 25× with MES Saline/0.1% NP40 containing either 1 mM 83/DMSO or DMSO alone. Samples were incubated a further 2 hours, then acidified to pH 5.0 for 5 minutes at RT and reneutralized. POST controls were then mixed with the appropriate concentration of compound. The equivalent amount of DMSO was added to all other samples. Reactions were precipitated as described above.

Calculation of Nonspecific Quenching

Apparent inhibition due to nonspecific effects was quantitated from the POST controls with the equation:

$$\text{observed cpm} = \text{true cpm} \cdot \text{quench factor}$$

where the quench factor is the fraction by which the compound reduces the cpm of the POST control compared to otherwise identical samples with compound omitted. The true cpm is the cpm that would be observed if quenching did not occur.

Calculation of % Inhibition

Inhibition was calculated as the % difference in cpm precipitated by a given sample compared to the cpm precipitated by the appropriate control sample. The % inhibition compensated for quenching was calculated as:

$$\text{true inhibition} = \left[1 - \frac{(1 - \text{inhibition})}{(1 - \text{inhibition}_{POST})}\right] \times 100\%$$

where inhibition is the observed inhibition in compound-containing samples and inhibition$_{POST}$ is the observed inhibition of compound-containing POST samples.

Calculation of IC$_{50}$

The IC$_{50}$, the concentration of ligand producing 50% specific inhibition, was determined for each of the derivatives of compound 83. The maximum inhibition corrected for quenching was 63.4±10.0%. Therefore, half-maximal inhibition occurs at 31.7%. The concentration at which each compound reduces the cpm precipitated by approximately 31.7% was determined from a plot of log concentration vs. % inhibition.

pH Control

This control tests whether the trial compounds altered the pH of the solutions. The acidification reactions were identical to the acidification reactions performed for SPA analysis, except that the detergent and radiolabeled protein were omitted. The pH of acidified compound-containing solutions was compared to that of the analogous DMSO-containing solution.

Hemagglutination

Serial 2-fold dilutions of inoculum in PBS were placed in a 96 well plate with V-shaped wells. An equal volume of 0.5% washed human red blood cells in PBS was added to each. Wells were covered and incubated at 4° C. After 4 hours the last well agglutinated was recorded.

Hemagglutinating units (HAU) are computed by the formula:

$$HAU/ml = 20 \times 2^{(n-1)}$$

where n is the last well agglutinated.

In testing compounds for inhibition of hemagglutination, the virus was incubated for 30 minutes at RT with 2×concentrations of ligand. Serial 2×dilutions of virus were done in a 2×solution of compound/PBS. Addition of the rbcs halved the compound concentration in each well.

Hemolysis (HEM)

Protocol 1

Human red blood cells (rbcs) were washed twice with PBS then suspended to 1% v/v with MES Saline. Approximately 1.5 µg X31 virus was mixed with trial compound and MES Saline in a final volume of 25 µl then incubated for 25 minutes at RT. Following addition of 225 µl 1% rbcs, the reaction was warmed to 37° C. for 5 minutes. The pH was lowered to 5.0 (unless otherwise noted) by addition of a predetermined amount of 1N HAc. The reaction was reneutralized with 1N NaOH after incubation for 5 minutes at 37° C. Intact rbcs were pelleted by centrifugation at 10,000×g for 3 minutes. The $OD_{570}$ was measured on 100 or 150 µl aliquots of supernatant. Background values were determined from identically treated samples lacking virus. Titrations demonstrated that the amount of virus used fell in the middle of the linear range.

Protocol 2

Protocol 2 is similar to Protocol 1 except that virus was preincubated with test compounds for 45 minutes at RT and rbcs were diluted from an 8% suspension. Reactions were incubated at low pH for 15 minutes at 37° C.

Protocol 3

Protocol 3 is similar to Protocol 1 except that the C22 strain of influenza X31 was used. Virus titrations determined that 0.6 µg of viral protein (by Lowry) gave an OD in the center of the linear range. Virus and compound were preincubated for 0.5 hr at RT in a volume of 100 µl. 350 µl of 1% washed rbcs were added. Warming, acidification, and reneutralization were done as in Protocol 1 except that the reaction was allowed to proceed for 15 mins at 37° C. $OD_{570}$ was determined as above.

Hb controls were identical to other reactions except that virus was replaced by the same volume of assay buffer and pre-lysed rbcs were used instead of intact rbcs. Rbcs were lysed in 10 mM MES, then centrifuged at 10,000×g for 5 minutes. The supernatant was diluted 1:20 with MES Saline.

Calculation of $IC_{50}$

The % reduction on OD in sample containing compounds were calculated as:

$$\left[1 - \frac{(OD_{DMSO,-} - OD_{DMSO,+})}{(OD_{-} - OD_{+})}\right] \times 100\%$$

where $OD_{DMSO,+}$ is the absorbance of samples containing DMSO (or the appropriate solvent), $OD_{DMSO,-}$ the background lysis of rbcs without virus present but with DMSO, $OD_{+}$ is the absorbance of the sample and virus containing samples and $OD_{-}$ the background lysis caused by the compound in the absence of virus. The $IC_{50}$ is defined as the concentration reducing the OD by the same amount as samples containing half the amount of virus. Depending on the day, 50% less virus reduced the OD by 25–60%.

Syncytia Formation: Fusion from Without

Influenza-mediated cell-cell fusion was induced following the previously described protocol for fusion from without. Doms, R. W., Gething, M. -J., Henneberry, J., White, J. and Helenius, A., "Variant influenza virus hemagglutinin 5 that induces fusion at elevated pH." *J. Virol.* 57: 603–13 (1986). 50–60% confluent plates of CV-1 cells were washed with cold PBS. A total of 1 ml DME, 100 mg/ml streptomycin, 100 U/ml penicillin (DME/P&S) with or without 6.5 µg of virus (by Lowry protein determination) and the appropriate concentration of trial compound was added to each well on ice. The final concentration of DMSO in all wells was 0.1% by volume. The plates were incubated at 4° C. for 1 hour with gentle agitation. Following the binding period, the virus solution was aspirated and replaced with prewarmed MSSH buffer, pH 5.2, containing compound and DMSO. The buffer was aspirated after incubation at 37° C. for 3 minutes. Cells were allowed to recuperate in CV-1 growth media for 4 hrs at 37°, 5% $CO_2$. Cells were examined for any alterations in cell morphology then stained for 30 minutes at RT with 0.2% crystal violet in 50% ethanol.

Infectivity Assay (INF)

This protocol is adapted from the CDC protocol. MDCK2 cells were seeded at 35,000 cells per well in 96 well cluster dishes and grown in MDCK growth media for 24 hrs at 37° C., 5% $CO_2$ C22 virus was preincubated with the appropriate concentration of test compound in MEM-EBSS, 100 mg/ml streptomycin, 100 U/ml penicillin for 25 mins at RT. All samples contained 0.67% v/v DMSO and 0–1.5 HAU virus per 100 µl. Cells were infected with 100 µl virus/compound/MEM-EBSS for 15 hrs at 37° C., 5% $CO_2$. Trypsin, normally included to cleave HA0 to HA, was omitted so only a single round of infection could occur. Cells were rinsed once with PBS then fixed with 80% acetone/PBS for 15 min at RT and allowed to air dry. Plates were washed with PBS/0.05% Tween 20 then blocked with EIA diluent (PBS, 1% FBS, 0.1% Tween 20) for 30 min at RT. Wells were incubated for 1 hr at 37° C. with site A monoclonal antibody diluted to 1:2000 with EIA diluent, washed 4 times with PBS/0.05% Tween 20, then incubated for 1 hr at 37° C. with F(ab)'-2-goat-anti-mouse Ig(G)-peroxidase (Boehringer Mannheim) diluted to 1:6000 with EIA diluent. Plates were washed 4 times more with PBS/0.05% Tween 20. A 0.3 mg/ml solution of 3,3', 5,5'-tetramethylbenzidine substrate (Sigma) was prepared in citrate-acetate buffer (0.1 M sodium acetate brought to pH 5.5 with 1.0 M citric acid) with 6% v/v DMSO and 0.005% $H_2O_2$. Color development was allowed to proceed for 10 min at RT, then was stopped by the addition of 2 M sulfuric acid. The $OD_{410}$ was measured for each well.

All samples were done in triplicate, and each concentration of trial compound was tested with at least two different concentrations of virus. A standard curve relating the amount of infecting virus (preincubated with the appropriate solvent) to $OD_{410}$ was determined from virus titrations on each plate. The amount of virus producing an OD equivalent to that observed in each compound-containing well was determined from the standard curve. % Inhibition is expressed as the % difference between that amount of virus and the input amount. The % inhibition was plotted as a function of log concentration. The $IC_{50}$, the concentration at which infectivity is reduced by 50%, was read off the graph.

MTT Viability Assay

Protocol 1

Infections of MDCK2 cells with virus, compounds, and DMSO were set up identically as for the EIA assay. Following the 15 hour incubation, test compounds were washed away with PBS. 50 µl of MDCK2 growth media and 25 µl 2 mg/ml 3-(4,5-dimethylthiazol-2-yl)-2,5-diphenyl tetrazolium bromide (Sigma) in PBS were added to each well. Plates were returned to 37° C., 5% $CO_2$ for 4 hrs. Crystals were broken up by vigorous mixing following addition of 80 µl isopropanol/0.04 N HCl. After incubation for 30 mins at RT, $OD_{570}$ was read on an ELISA reader. % Inhibition is the % reduction of $OD_{570}$ in the wells infected with compound compared to otherwise identical samples with compound omitted. This assay has been published elsewhere. Mosmann, T., "Rapid colorimetric assay for cellular growth and survival: application to proliferation and cytotoxicity assays," *J. Immunol. Methods* 65: 55–63 (1983).

Protocol 2

CV-1 cells were plated in 96 well tissue culture dishes at 10,000 cells per well and grown in CV-1 growth media for 24 hrs. The appropriate concentration of compound in DME/P&S with 0.6% DMSO was added and incubated for 1 hour at 4° C. with constant tilting. Following the binding period, cells were examined for any observable changes in morphology. Cells were rinsed twice with PBS then incubated with 25 μl 2 mg/ml MTT in PBS and 50 μl DME/P&S. Plates were incubated and processed for spectrophotometry as in Protocol 1.

DOCK

Overview

The DOCK package of computer programs identifies invaginations on a receptor surface, orients small molecules in a site of interest, and scores each ligand by the degree it complements the shape and/or electrostatic properties of the site. DOCK requires three-dimensional coordinates of both ligand and receptor, and treats both molecules as rigid bodies. Summaries of the programs comprising the DOCK package and the differences between versions 1 and 2 are presented here. The algorithms are described in detail elsewhere. Kuntz, I. D., Blaney, J. M., Oatley, S. J., Langridge, R. and Ferrin, T. E., "A geometric approach to macromolecule-ligand interactions," *J. Mol. Biol.* 161: 269–88 (1982); Shoichet, B. K., Bodian, D. L. and Kuntz, I. D., "Molecular docking using shape descriptors," *J. Comp. Chem.* 13: 380–97 (1992).

Site Characterization: Sphere Generation

The program SPHGEN builds spheres analytically from the molecular surface of a receptor. Kuntz, I. D. et al., loc. cit. The radii of the spheres is proportional to the concavity of the surface: flat regions are represented by larger spheres while small spheres are generated in highly featured regions. A set of heuristics reduces the number of spheres from one per surface point to one per site atom. A single linkage algorithm identifies sets of overlapping spheres ("clusters"), each of which represents a potential binding site.

In DOCK_2.0 and later versions, the option to tailor the clusters has been included. The program CLUSTER allows the user to define alternate means of paring the unpruned set of SPHGEN spheres. Shoichet, B. K. et al., loc. cit.

Generation and Evaluation of Ligand Orientations

DOCK uses the sphere definition of a target site to guide the positioning of ligands. Kuntz, I. D. et al., loc. cit. Shoichet, B. K. et al., loc. cit. While the details of the algorithm have changed significantly between versions 1 and 2 the basic principle has been maintained. Sphere centers indicate possible positions for ligand atoms in the site. Selected ligand atoms are mapped onto subsets of sphere centers with internal distances approximating those of the ligand atoms. Each mapping of ligand atoms onto appropriate sphere centers defines a transformation matrix that orients the small molecule in the site. A minimum of four atom-sphere center pairs are required to define a unique configuration. Although thousands of orientations are typically found for each small molecule, the search is non-exhaustive.

Following transformation of the ligand coordinates into the receptor site, the orientation is scored by evaluating the extent of shape complementarity between the receptor and the ligand. The scoring function approximates a van der Waals interaction energy. Ligand atoms docked within attractive distances of receptor atoms are assigned positive scores. Orientations in which ligand atoms overlap receptor atoms are assigned negative scores and discarded. In DOCK_1, the score for each orientation is a function of the pairwise distances between each ligand atom and each receptor atom. In DOCK_2 and later versions, the program DISTMAP pre-scores a grid over the receptor site. Shoichet, B. K. et al., loc. cit. The score for each orientation is the sum of the scores of the grid points nearest each ligand atom. DISTMAP allows different distance parameters to be used for polar and nonpolar site atoms.

DOCK may be run in two modes, SEARCH and SINGLE. In SINGLE mode one ligand is oriented in the site and every acceptable configuration is retained. In SEARCH mode, DOCK reads a database of structures. Each ligand is docked in thousands of orientations, but only the highest scoring orientation is saved. The ligands are ranked by their top score, and a list of the highest scoring ligands is produced.

Databases

MACCS (Molecular Design, Ltd.) provides CONCORD (Tripos)-generated structures of compounds from the Fine Chemicals Directory, Comprehensive Medicinal Chemistry, and Molecular Drug and Data Report. Revision 1.0 and the 1989 databases were used. Charges were calculated for each of the chemicals using the method of Gasteiger and Marsili as incorporated into SYBYL (Tripos). Gasteiger, J. and Marsili, M., "Iterative partial equalization of orbital electronegativity—a rapid access to atomic charges," *Tetrahedron* 36: 3219–88 (1980). Crystallographic coordinates of the soluble ectodomain of X31 hemagglutinin (BHA) have been deposited as entry 1hmg in the Brookhaven Protein Data Bank (PDB). Wilson, I. A. et al., *Nature*, loc. cit., Abola, E. E., Bernstein, F. C., Bryant, S. H., Koetzle, T. F. and Weng, J., In F. H. Allen, G. Bergerhoff and R. Seivers (Eds.), *Crystallographic Databases—Information Content, Software Systems. Scientific Applications,* (Data Commission of the International Union of Crystallography, Cambridge, 1987) pp. 107–132; Bernstein, F. C., Koetzle, T. F., Williams, G. J. B., Meyer, E. F., Jr., Brice, M. D., Rodgers, J. R., Kennard, O., Shimanouchi, T., et al., "The Protein Data Bank: A computer-based archival file for macromolecular structures," *J. Mol. Biol.* 112: 535–42 (1977).

Hardware and Other Software

Molecular surfaces were computed on SUN3 workstations with DMS, a distributed processing implementation of Connolly's molecular surface algorithm.

Connolly, M. L., "Solvent-accessible surfaces of proteins and nucleic acids," *Science* 221:709–13 (1983). The DMS program was developed by Conrad Huang at the UCSF Computer Graphics Laboratory. The DMS and MIDAS-PLUS programs are available through the UCSF Computer Graphics Laboratory. Computer graphics software MIDAS and its successor, MIDASPLUS, were run on Silicon Graphics IRIS workstations. Ferrin, T. E., Huang, C. C., Jarvis, L. E. and Langridge, R., "The Midas display system," *J. Mol. Graph.* 6: 13–27 (1988).

Purification and Synthesis of Derivatives of Compound 83

83K—4A,5,8,8A-tetrahydro-5,8-methano-1,4-naphthoguinone

The commercial compound was recrystallized twice from hexane. The structure was confirmed by H-NMR and IR. In the IR there were no OH bands but strong carbonyl bands centered at 1600 cm$^{-1}$.

Elem Anal Calc'd: C 75.84%, H 5.79%. Found: C 75.75%, H 5.80%.

83A—5,8-dihydro-5,8-methano-1,4-naphthalenediol

Prepared from 83K by the method of Porter et al. Porter, R. F., Rees, W. W., Frauenglass, E., Wilgus, H. S., Nawn, G. H., Chiesa, P. P. and Gates, J. W., "The chemistry of thioether-substituted hydroquinones and quinones. I. The 1,4 addition of a heterocyclic mercaptan to quinones," *J. Org. Chem.* 29: 588–94 (1964). The crude product was purified by flash chromatography on silica gel, using acetone:hexane (1:3, v/v) as the eluent, to afford pure 83A as pale-tan rosette crystals. Still, W. C., Kahn, M. and Mitra, A., "Rapid chromatographic technique for preparative separations with moderate resolution," *J. Org. Chem.* 43: 2923–25 (1978). The structure was confirmed by H-NMR and IR (no carbonyl bands but strong OH band).

Elem anal Calc'd: C 75.84%, H 5.79%. Found: C 75.62%, H 5.66%.

TABLE 8

Summary of purification and characterization of several derivatives of compound 83. Literature and experimental melting points are compared. The method of purification, and summaries of the elemental analysis and NMR experiments are given. Details of the elemental analysis are in Table 9.

| compound | purification | elem. anal | mp (° C.) | lit mp (° C.) | NMR |
|---|---|---|---|---|---|
| 90 | recryst. Et$_2$O | passed | 124–125 | 124–125 | ok |
| 99 | sublim | passed | 223–225 | 223–225 | ok |
| 111 | as is | passed | 178–180 | 180 | ok |
| 114 | sublim | passed | 218 dec | 216–218 | ok |
| 116 | sublim | passed | 216.5–217.5 sub | 217 sub | ok |
| 117 | as is | passed | 126.5–128 | 127–129 | ok |
| 118 | as is | passed | 105.5–106.5 | 107 | ok |
| 119 | recryst. CHCl$_3$—EtOH | passed | 160–163 | 161–163 | ok |
| 120 | recryst. EtOH—HOAc | passed | 193–195 | 191–192 | ok |
| 121 | recryst.. HCl(aq)—SnCl$_2$ | passed as ¼H$_2$O | — | | ok |
| 125 | recryst.. HCl(aq)—SnCl$_2$ | failed twice | 236 dec | — | ok |
| 126 | recryst.. MeNO$_2$ | passed | 260–262 dec | 259–261 dec | ok |

Structures of compounds 101, 102, 103, 104, 108 were confirmed by H-NMR. TLC analysis showed commercial samples of 91 and 97 are complex mixtures.

TABLE 9

Summary of elemental analysis results. The experiment was repeated twice with compound 121. Compound 125 failed this test.

| compound | calculated | found |
|---|---|---|
| 90 | C 75.94%, H 3.82% | C 75.84%, H 3.94% |
| 99 | C 69.54%, H 7.30% | C 69.78%, H 7.32% |
| 111 | C 74.97%, H 6.86% | C 74.77%, H 7.03% |
| 114 | C 80.75%, H 3.87% | C 80.99%, H 3.97% |
| 116 | C 69.54%, H 7.30% | C 69.78%, H 7.32% |
| 117 | C 72.25%, H 8.49% | C 72.46%, H 8.55% |
| 118 | C 76.73%, H 4.68% | C 76.60%, H 4.70% |
| 119 | C 68.96%, H 3.47% | C 69.19%, H 3.60% |
| 120 | C 68.96%, H 3.47% | C 68.96%, H 3.59% |
| 121 (· ¼H$_2$O) | C 60.00%, H 5.30%, N 7.00%, Cl 17.71% | C 60.39%, H 5.27%, N 6.67%, Cl 17.52% C 60.23%, H 5.28%, N 6.59% |
| 125 | — | — |
| 126 | C 74.98%, H 5.03% | C 74.67%, H 5.15% |

The method of a preferred form of practicing the present invention has been disclosed but one skilled in the art will recognize additional compounds that can be used with the present method that come within the present teachings and claims.

What is claimed is:

1. A method of treating a viral condition caused by an enveloped virus, said method comprising using a therapeutically effective amount of a compound selected from the group consisting of a substituted benzene, wherein said benzene comprises a 2-R$^1$, 3-R$^2$-1-OX$^1$, 4-OX$^2$ compound where at least one of R$^1$ and R$^2$ include a carbon linkage to the benzene ring and OX$^1$ and OX$^2$ are simultaneously hydroxy.

2. The method of claim 1 wherein said virus is influenza, subclass A.

3. The method of claim 1 wherein said virus is influenza, subclass B.

4. The method of claim 1 wherein said virus is influenza, subclass C.

5. The method of claim 1 wherein R$^1$ is a hydrocarbon moiety of one to ten carbons.

6. The method of claim 1 wherein R$^2$ is a hydrocarbon moiety of one to ten carbons.

7. The method of claim 1 wherein R$^1$ is —CH$_2$—O—R$^3$ and R$^3$ is a hydrocarbon moiety of one to ten carbons.

8. The method of claim 1 wherein R$^1$ is tert-butyl and R$^2$ is hydrogen.

9. The method of claim 1 wherein one hydrogen of one hydroxyl of said diol is substituted with a hydrocarbon moiety of one to six carbons.

10. The method of claim 1 further comprising preventing said viral condition using a therapeutically effective amount of said compound.

11. A method of treating a viral condition caused by an enveloped virus, said method comprising using a therapeutically effective amount of a compound having an IC$_{50}$ of less than 10$^{-3}$ M in the INF assay, wherein said compound comprises a substituted benzene, wherein said benzene comprises a 2-R$^1$, 3-R$^2$-1-OX$^1$, 4-OX$^2$ compound where at least one of R$^1$ and R$^2$ include a CH$_2$ linkage to the benzene ring and OX$^1$ and OX$^2$ are simultaneously hydroxy.

12. The method of claim 11 further comprising preventing said viral condition using a therapeutically effective amount of said compound.

13. A method of treating a viral condition caused by an enveloped virus, said method comprising using a therapeutically effective amount of tert-butylhydroquinone.

14. The method of claim 13 wherein said viral condition is influenza.

15. A method of treating a viral condition caused by an enveloped virus, said method comprising using a therapeutically effective amount of a compound which binds near the hinge region or near the stem region of hemagglutinin.

16. The method of claim 15 wherein said compound binds near the region of Asn 296A; Tyr 308A, Val 309A, Lys 310A, Gln 311A, Asn 312A, Glu 85B, Asp 86B, Thr 87B, Lys 88B, Ile 89B, Asp 90B, Leu 91B, Trp 92B, Ser93B, Try 94B, Asn 95B, Ala 96B, Glu 97B, Leu 98B, Leu 99B, Pro 293C, Phe 294C, Gln 295C, Gly 303C, Ala 304C, Cys 305C, Pro 306C, Lys 307C, Tyr 308C, Val 309C, Lys 58D, Thr 59D, Asn 60D, Glu 61D, Lys 62D, Thr 87D, Lys 88D, Ile 89D, Asp 90D, Leu 91D, Trp 92D, Ser 93D, Tyr 94D, Asn 95D, Ala 96D and Leu 99D.

17. The method of claim 15 wherein said compound binds near the region of Cys14A, Leu 15A, Gly 16A, His 18A, Glu 325A, Ile 10B, Glu 11B, Asn 12B, Gly 13B, Trp 14B, Arg 25B, Asn 135B, and Cys 137B.

18. A method of treating a viral condition wherein the viral condition is caused by a virus having a fusion protein which has a native, non-fusogenic conformation and a second, fusogenic conformation, the method comprising using a therapeutically effective amount of a compound which binds to the fusion protein in the native conformation and reduces the ability of the fusion protein to adopt the fusogenic conformation.

19. The method of claim 18 wherein said compound is selected from the group consisting of a substituted benzene, wherein said benzene comprises a 2-R$^1$, 3-R$^2$-1-OX$^1$, 4-OX$^2$ compound where at least one of R$^1$ and R$^2$ include a carbon linkage to the benzene ring and OX$^1$ and OX$^2$ are simultaneously hydroxy.

20. The method of claim 18 wherein said compound comprises tert-butylhydroquinone.

21. The method of claim 18 wherein said viral condition is caused by a virus from a family in the group consisting of Togaviridae, Flaviviridae, Coronaviridae, Rhabdoviridae, Filoviridae, Paramyxoviridae, Orthomyxoviridae, Bunyaviridae, Arenaviridae, Retroviridae, Hepadnaviridae, Herpesviridae, Poxviridae and Iridoviridae.

22. The method of claim 18 wherein said viral condition is caused by a virus in the group consisting of rubella, yellow fever, rabies, influenza, Korean hemorrhagic fever, common colds, respiratory syncytial virus, measles, mumps, HIV, hepatitis B, Herpes simplex, CMV, chicken pox, smallpox, Marburg virus, Lassa fever and African swine fever.

23. A method of treating a viral condition caused by an enveloped virus, said method comprising using a therapeutically effective amount of a compound selected from the group consisting of a substituted benzene, wherein said benzene comprises a 2-$R^1$, 3-$R^2$-1-$OX^1$, 4-$OX^2$ compound where at least one of $R^1$ and $R^2$ include a carbon linkage to the benzene ring and wherein one of $OX^1$ and $OX^2$ is selected from the group consisting of hydroxy and oxo and the other is $OR^4$ where $R^4$ is a saturated or unsaturated hydrocarbon of less than four carbons.

24. A method of treating a viral condition caused by an enveloped virus, said method comprising using a therapeutically effective amount of a compound having an $IC_{50}$ of less than $10^{-3}$ M in the INF assay, wherein said compound comprises a substituted benzene, wherein said benzene comprises a 2-$R^1$, 3-$R^2$-1-$OX^1$, 4-$OX^2$ compound where at least one of $R^1$ and $R^2$ include a $CH_2$ linkage to the benzene ring and wherein one of $OX^1$ and $OX^2$ is selected from the group consisting of hydroxy and oxo and the other is $OR^4$ where $R^4$ is a saturated or unsaturated hydrocarbon of less than four carbons.

25. A method of treating a viral condition wherein the viral condition is caused by a virus having a fusion protein which has a native, non-fusocienic conformation and a second, fusogenic conformation, the method comprising using a therapeutically effective amount of a compound which binds to the fusion protein in the native conformation and reduces the ability of the fusion protein to adopt the fusogenic conformation wherein said compound is a substituted benzene, comprising a 2-$R^1$, 3-$R^2$-1-$OX^1$, 4-$OX^2$ compound where at least one of $R^1$ and $R^2$ include a carbon linkage to the benzene ring and wherein one of $OX^1$ and $OX^2$ is selected from the group consisting of hydroxy and oxo and the other is $OR^4$ where $R^4$ is a saturated or unsaturated hydrocarbon of less than four carbons.

26. The method of claim 1 wherein said compound is the tautomeric ene-dione form of said substituted benzene.

27. The method of claim 24 wherein said compound is the tautomeric ene-dione form of said substituted benzene.

28. The method of claim 25 wherein said compound is the tautomeric ene-dione form of said substituted benzene.

* * * * *